(12) United States Patent
Borisevich

(10) Patent No.: US 12,235,154 B2
(45) Date of Patent: Feb. 25, 2025

(54) MAINTAINING CONSISTENT PHOTODETECTOR SENSITIVITY IN AN OPTICAL MEASUREMENT SYSTEM

(71) Applicant: HI LLC, Los Angeles, CA (US)

(72) Inventor: Alex Borisevich, Lancaster, CA (US)

(73) Assignee: HI LLC, Culver City, CA (US)

(*) Notice: Subject to any disclaimer, the term of this patent is extended or adjusted under 35 U.S.C. 154(b) by 393 days.

(21) Appl. No.: 17/724,628

(22) Filed: Apr. 20, 2022

(65) Prior Publication Data

US 2022/0397453 A1  Dec. 15, 2022

Related U.S. Application Data

(60) Provisional application No. 63/255,483, filed on Oct. 14, 2021, provisional application No. 63/210,974, filed on Jun. 15, 2021.

(51) Int. Cl.
*G01J 1/08* (2006.01)
*G01J 1/02* (2006.01)
*G06F 1/16* (2006.01)
*H01L 31/107* (2006.01)

(52) U.S. Cl.
CPC .............. *G01J 1/08* (2013.01); *G06F 1/163* (2013.01); *H01L 31/107* (2013.01); *G01J 2001/0257* (2013.01)

(58) Field of Classification Search
CPC .... G01J 1/08; G01J 2001/0257; G01J 1/0219; G01J 2001/442; G06F 1/163; H01L 31/107; H01L 31/167; A61B 5/0261; A61B 5/14553; A61B 5/6803; A61B 2562/0238; A61B 2562/046

See application file for complete search history.

(56) References Cited

U.S. PATENT DOCUMENTS

| 5,853,370 A | 12/1998 | Chance et al. |
| 6,240,309 B1 | 5/2001 | Yamashita et al. |
| 6,384,663 B2 | 5/2002 | Cova et al. |
| 6,640,133 B2 | 10/2003 | Yamashita |
| 6,683,294 B1 | 1/2004 | Herbert et al. |
| 7,356,365 B2 | 4/2008 | Schurman |

(Continued)

FOREIGN PATENT DOCUMENTS

WO  2018033751  2/2018

OTHER PUBLICATIONS

Alayed, et al., "Characterization of a Time-Resolved Diffuse Optical Spectroscopy Prototype Using Low-Cost, Compact Single Photon Avalanche Detectors for Tissue Optics Applications", Sensors 2018, 18, 3680; doi:10.3390/s18113680, Oct. 29, 2018.

(Continued)

*Primary Examiner* — Georgia Y Epps
*Assistant Examiner* — Monica T Taba
(74) *Attorney, Agent, or Firm* — ALG Intellectual Property, LLC

(57) ABSTRACT

An illustrative optical measurement system includes a light source configured to emit a light pulse directed at a target. The optical measurement system further includes a control circuit configured to drive the light source with a current pulse comprising a non-linear rise, and a decline from a maximum output to zero having a duration within a threshold percentage of a total pulse duration of the current pulse.

35 Claims, 23 Drawing Sheets

(56) References Cited

U.S. PATENT DOCUMENTS

| | | |
|---|---|---|
| 7,547,872 B2 | 6/2009 | Niclass et al. |
| 7,774,047 B2 | 8/2010 | Yamashita et al. |
| 8,026,471 B2 | 9/2011 | Itzler |
| 8,078,250 B2 | 12/2011 | Chen et al. |
| 8,082,015 B2 | 12/2011 | Yodh et al. |
| 8,633,431 B2 | 1/2014 | Kim |
| 8,817,257 B2 | 8/2014 | Herve |
| 9,058,081 B2 | 6/2015 | Baxter |
| 9,076,707 B2 | 7/2015 | Harmon |
| 9,131,861 B2 | 9/2015 | Ince et al. |
| 9,316,735 B2 | 4/2016 | Baxter |
| 9,401,448 B2 | 7/2016 | Bienfang et al. |
| 9,419,635 B2 | 8/2016 | Kumar et al. |
| 9,442,201 B2 | 9/2016 | Schmand et al. |
| 9,529,079 B1 | 12/2016 | Droz |
| 9,574,936 B2 | 2/2017 | Heinonen |
| 9,946,344 B2 | 4/2018 | Ayaz et al. |
| D817,553 S | 5/2018 | Aaskov et al. |
| D825,112 S | 8/2018 | Saez |
| 10,158,038 B1 | 12/2018 | Do Valle et al. |
| 10,340,408 B1 | 7/2019 | Katnani |
| 10,424,683 B1 | 9/2019 | Do Valle |
| 10,515,993 B2 | 12/2019 | Field et al. |
| 10,697,829 B2 | 6/2020 | Delic |
| 10,772,561 B2 | 9/2020 | Donaldson |
| 10,809,796 B2 | 10/2020 | Armstrong-Muntner |
| 10,912,504 B2 | 2/2021 | Nakaji |
| 11,006,876 B2 | 5/2021 | Johnson |
| 11,006,878 B2 | 5/2021 | Johnson |
| 2001/0043093 A1* | 11/2001 | Sakura ............. H04B 10/508 327/108 |
| 2007/0083097 A1 | 4/2007 | Fujiwara |
| 2009/0012402 A1 | 1/2009 | Mintz |
| 2011/0208675 A1 | 8/2011 | Shoureshi et al. |
| 2013/0342835 A1 | 12/2013 | Blacksberg |
| 2014/0191115 A1 | 7/2014 | Webster et al. |
| 2014/0217264 A1 | 8/2014 | Shepard |
| 2014/0275891 A1 | 9/2014 | Muehlemann et al. |
| 2015/0038811 A1 | 2/2015 | Asaka |
| 2015/0041625 A1 | 2/2015 | Dutton |
| 2015/0054111 A1 | 2/2015 | Niclass et al. |
| 2015/0077279 A1 | 3/2015 | Song |
| 2015/0150505 A1 | 6/2015 | Kaskoun et al. |
| 2015/0327777 A1 | 11/2015 | Kostic et al. |
| 2015/0364635 A1 | 12/2015 | Bodlovic et al. |
| 2017/0030769 A1 | 2/2017 | Clemens et al. |
| 2017/0052065 A1 | 2/2017 | Sharma et al. |
| 2017/0176596 A1 | 6/2017 | Shpunt et al. |
| 2017/0179173 A1 | 6/2017 | Mandai et al. |
| 2017/0202518 A1 | 7/2017 | Furman et al. |
| 2017/0281086 A1 | 10/2017 | Donaldson |
| 2017/0363467 A1 | 12/2017 | Clemens et al. |
| 2017/0367650 A1 | 12/2017 | Wallois |
| 2018/0014741 A1 | 1/2018 | Chou |
| 2018/0027196 A1 | 1/2018 | Yang et al. |
| 2018/0039053 A1 | 2/2018 | Kremer et al. |
| 2018/0070830 A1 | 3/2018 | Sutin et al. |
| 2018/0070831 A1 | 3/2018 | Sutin et al. |
| 2018/0089848 A1 | 3/2018 | Yang et al. |
| 2019/0025406 A1* | 1/2019 | Krelboim ............. H01S 5/062 |
| 2019/0113385 A1 | 4/2019 | Fukuchi |
| 2019/0175068 A1 | 6/2019 | Everdell |
| 2019/0355861 A1 | 11/2019 | Katnani |
| 2019/0363210 A1 | 11/2019 | Do Valle |
| 2019/0388018 A1 | 12/2019 | Horstmeyer |
| 2020/0060542 A1* | 2/2020 | Alford ............. A61B 5/0066 |
| 2020/0116838 A1 | 4/2020 | Erdogan |
| 2020/0196932 A1 | 6/2020 | Johnson |
| 2020/0253479 A1 | 8/2020 | Nurmikko |
| 2020/0315510 A1 | 10/2020 | Johnson |
| 2020/0337624 A1 | 10/2020 | Johnson |
| 2020/0390358 A1 | 12/2020 | Johnson |

OTHER PUBLICATIONS

Arslan, et al., "Power Efficient Current Driver Based on Negative Boosting for High-Speed Lasers", Electronics 2019, 8, 1309; doi:10.3390/electronics8111309, 2019.

Ashok, et al., "Optimum electrical pulse characteristics for efficient gain switching in QCL", Optik—International Journal for Light and Electron Optics http://dx.doi.org/10.1016/j.ijleo.2017.08.071, 2017.

Ban, et al., "Kernel Flow: a high channel count scalable TD-fNIRS system", https://www.spiedigitallibrary.org/conference-proceedings-of-spie Proc. of SPIE vol. 11663, 116630B doi: 10.1117/12.2582888, Mar. 5, 2021.

Ban, et al., "Kernel Flow: a high channel count scalable time-domain functional near-infrared spectroscopy system", https://www.spiedigitallibrary.org/journals/Journal-of-Biomedical-Optics on Jan. 18, 2022.

Contini, et al., "Photon migration through a turbid slab described by a model based on diffusion approximation. I. Theory", Appl. Opt. 36(19), 4587 (1997).

Di Capua, et al., "A Novel Method to Predict the Real Operation of Ferrite Inductors with Moderate Saturation in Switching Power Supplies Applications", IEEE, Jun. 2016, Digital Object Identifier 10.1109/TPEL.201x.xxxxxxx.

Di Sieno, et al., "Probe-hosted large area silicon photomultiplier and high-throughput timing electronics for enhanced performance time-domain functional near-infrared spectroscopy", Biomed. Opt. Express 11(11), 6389 (2020).

Fishburn, et al., "Temporal Derivative Distribution Repair (TDDR): A motion correction method for fNIRS", Neuroimage. Jan. 1, 2019; 184: 171-179. doi:10.1016/j.neuroimage.2018.09.025.

Huikari, et al., "High-Energy Picosecond Pulse Generation by Gain Switching in Asymmetric Waveguide Structure Multiple Quantum Well Lasers", IEEE Journal of Selected Topics in Quantum Electronics, vol. 21, No. 6, Nov./Dec. 2015.

Huppert, et al., "HomER: a review of time-series analysis methods for near-infrared spectroscopy of the brain", Appl. Opt. 48(10), D280 (2009).

Kienle, et al., "Improved solutions of the steady-state and the time-resolved diffusion equations for reflectance from a semi-infinite turbid medium", J. Opt. Soc. Am. A 14(1), 246 (1997).

Konugolu, et al., "Broadband (600-1350 nm) Time-Resolved Diffuse Optical Spectrometer for Clinical Use", IEEE Journal of Selected Topics in Quantum Electronics, vol. 22, No. 3, May/Jun. 2016.

Krishna, et al., "Study of Gain Switching in Vertical Cavity Surface Emitting Laser under Different Electrical Pulse Inputs", Defence Science Journal, vol. 70, No. 5, Sep. 2020, pp. 538-541, DOI : 10.14429/dsj.70.16340.

Lacerenza, et al., "Wearable and wireless time-domain near-infrared spectroscopy system for brain and muscle hemodynamic monitoring", Biomed. Opt. Express 11(10), 5934 (2020).

Lange, et al., "Clinical Brain Monitoring with Time Domain NIRS: A Review and Future Perspectives", Applied Sciences 9(8), 1612 (2019).

Lange, et al., "MAESTROS: A Multiwavelength Time-Domain NIRS System to Monitor Changes in Oxygenation and Oxidation State of Cytochrome-C-Oxidase", IEEE J. Select. Topics Quantum Electron. 25(1), 1-12 (2019).

Li, et al., "Step-Pulse Modulation of Gain-Switched Semiconductor Pulsed Laser", Appl. Sci. 2019, 9, 602; doi:10.3390/app9030602, 2019.

Liero, et al., "GaN Laser Driver Switching 30 A in the Sub-Nanosecond Range", Proceedings of the 11th European Microwave Integrated Circuits Conference, Oct. 3-4, 2016, 978-2-87487-044-6.

Ma, et al., "A Digital-Type GaN Driver with Current-Pulse-Balancer Technique Achieving Sub-Nanosecond Current Pulse Width for High-Resolution and Dynamic Effective Range LiDAR System", 2019 IEEE International Solid-State Circuits Conference 978-1-5386-8531-0/19, 2019.

Martelli, et al., "Optimal estimation reconstruction of the optical properties of a two-layered tissue phantom from time-resolved single-distance measurements", Journal of Biomedical Optics 20(11), 115001 (Nov. 2015).

(56) References Cited

OTHER PUBLICATIONS

Mora, et al., "Fast silicon photomultiplier improves signal harvesting and reduces complexity in time-domain diffuse optics", Opt. Express 23(11), 13937 (2015).

Naidu, et al., "Optimal Control Systems", ISBN 0-8493-0892-5, p. 53-54, 2004.

Nissinen, et al., "A High Repetition Rate CMOS Driver for High-Energy Sub-ns Laser Pulse Generation in SPAD-Based Time-of-Flight Range Finding", IEEE Sensors Journal, vol. 16, No. 6, Mar. 15, 2016.

Pifferi, et al., "Performance assessment of photon migration instruments: the MEDPHOT protocol", Applied Optics, 14(11), 2104-2114, 2005.

Prahl, et al., "Optical Absorption of Hemoglobin", http://omlc.ogi.edu/spectra/hemoglobin/index.html, 1999.

Re, et al., "Multi-channel medical device for time domain functional near infrared spectroscopy based on wavelength space multiplexing", Biomed. Opt. Express 4(10), 2231 (2013).

Renna, et al., "Eight-Wavelength, Dual Detection Channel Instrument for Near-Infrared Time-Resolved Diffuse Optical Spectroscopy", IEEE J. Select. Topics Quantum Electron. 25(1), 1-11 (2019).

Slipchenko, et al., "High peak optical power of 1ns pulse duration from laser diodes—low voltage thyristor vertical stack", vol. 27, No. 22 / Oct. 28, 2019 / Optics Express 31446.

Torricelli, et al., "Time domain functional NIRS imaging for human brain mapping", NeuroImage 85, 28-50 (2014).

Wabnitz, et al., "Depth-selective data analysis for time-domain fNIRS: moments vs. time windows", Biomed. Opt. Express 11(8), 4224 (2020).

Wabnitz, et al., "Performance assessment of time-domain optical brain imagers, part 1: basic instrumental performance protocol", Journal of Biomedical Optics 19(8), 086010 (Aug. 2014).

Wabnitz, et al., "Performance assessment of time-domain optical brain imagers, part 2: nEUROPt protocol", Journal of Biomedical Optics 19(8), 086012 (Aug. 2014).

Wojtkiewicz, et al., "Self-calibrating time-resolved near infrared spectroscopy", Biomed. Opt. Express 10(5), 2657 (2019).

Zeng, et al., "A Compact Low=Power Driver Array for VCSELs in 65-nm CMOS Technology", IEEE Transactions on Nuclear Science, vol. 64, No. 6, pp. 1599-1604, Jun. 2017, doi: 10.1109/TNS.2017.2702064.

Zucchelli, et al., "Method for the discrimination of superficial and deep absorption variations by time domain fNIRS", 2013 OSA Dec. 1, 2013 | vol. 4, No. 12 | DOI:10.1364/BOE.4.002893 | Biomedical Optics Express 2893, 2013.

* cited by examiner

MAINTAINING CONSISTENT PHOTODETECTOR SENSITIVITY IN AN OPTICAL MEASUREMENT SYSTEM

RELATED APPLICATIONS

The present application claims priority under 35 U.S.C. § 119(e) to U.S. Provisional Patent Application No. 63/255,483, filed on Oct. 14, 2021, and to U.S. Provisional Patent Application No. 63/210,974, filed on Jun. 15, 2021, each of which is incorporated herein by reference in its entirety.

BACKGROUND INFORMATION

An optical measurement device may detect blood oxygenation levels and/or blood volume levels by measuring the change in shape of laser pulses after they have passed through target tissue, e.g., brain, muscle, finger, etc. The shape of laser pulses may include a temporal shape, as represented for example by a histogram generated by a time-to-digital converter (TDC) coupled to an output of a photodetector. A photodetector capable of detecting a single photon (i.e., a single particle of optical energy) is an example of a non-invasive detector that can be used in an optical measurement system to detect blood oxygenation levels and/or blood volume levels. An exemplary photodetector is implemented by a semiconductor-based single-photon avalanche diode (SPAD), which is capable of capturing individual photons with very high time-of-arrival resolution (a few tens of picoseconds).

The laser pulses may be generated by a laser diode that is driven by a circuit to generate narrow optical pulses with a high repetition rate. The electrical-to-optical efficiency of such circuits may typically be low.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
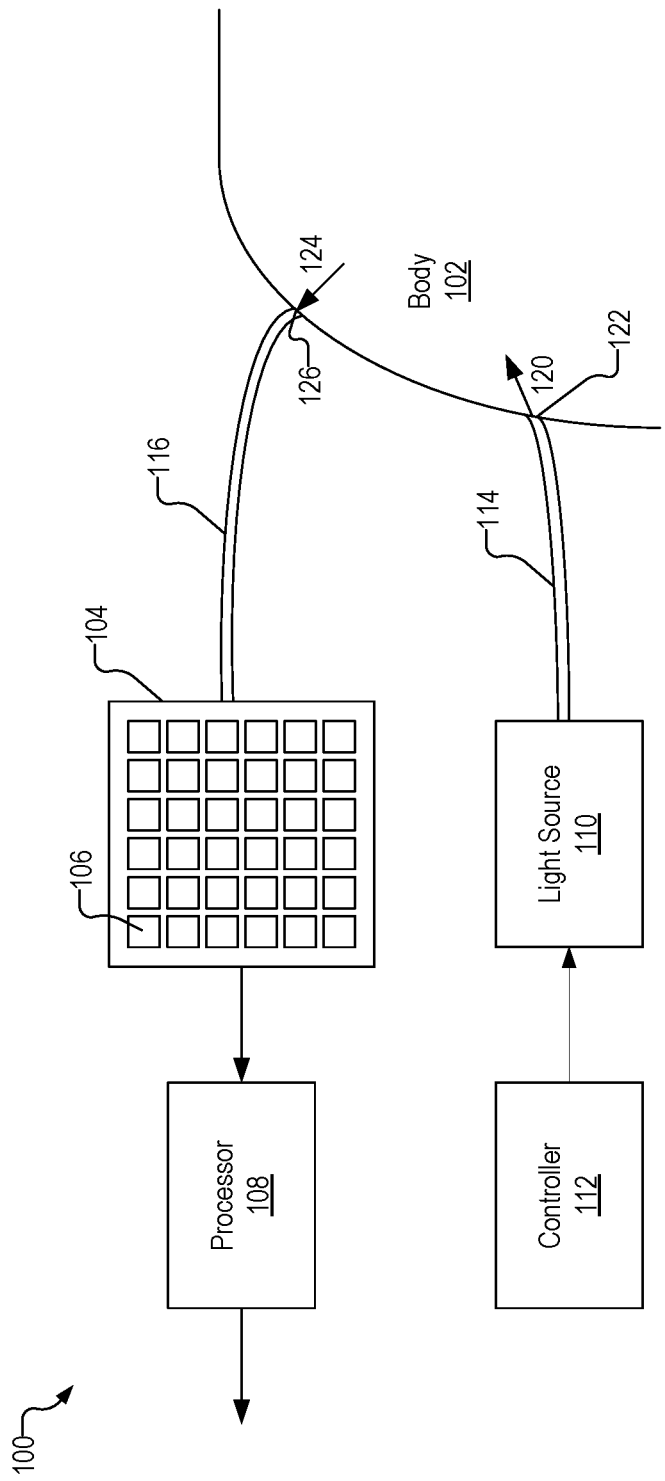
FIG. 1 shows an exemplary optical measurement system.

An optical measurement system as described herein may include a light source configured to emit a light pulse directed at a target within the body. The systems may further include a control circuit configured to drive the light source with a current pulse. A shape of the current pulse may determine an electrical-to-optical efficiency of the control circuit in driving the light source, especially with narrow optical pulses and a high repetition rate. An optimal current pulse shape may be determined by an optimal current pulse equation. Thus, control circuits that are configured to output current pulses similar to the optimal current pulse may be more efficient than conventional control circuits.

The systems, circuits, and methods described herein may be configured to drive light sources with current pulses that are similar to (e.g., within a threshold variance from) an optimal current pulse. For example, an optical measurement system may include a light source configured to emit a light pulse directed at a target. The optical measurement system may further include a control circuit configured to drive the light source with a current pulse comprising a non-linear rise, and a decline from a maximum output to zero having a duration within a threshold percentage of a total pulse duration of the current pulse.

Such control circuits may be more efficient than conventional control circuits, allowing for improved battery life. Further, more efficient control circuits may result in less power dissipation and consequently less temperature fluctuation during usage, which may result in more stable parameters for the light source. Such light source parameter stability may allow for more accurate measurements and more useful metrics and predictions (e.g., of mental states of a user, blood oxygenation levels of the user, etc.) based on histogram data generated by these measurements.

Mental states described herein refer to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, physiological functions, behavior, preferences, or attitude of the user, and the creation, training, and use of neuromes can be found in U.S. patent application Ser. No. 17/188,298, filed Mar. 1, 2021, issued as U.S. Pat. No. 11,132,625. Exemplary measurement systems and methods using biofeedback for awareness and modulation of mental state are described in more detail in U.S. patent application Ser. No. 16/364,338, filed Mar. 26, 2019, issued as U.S. Pat. No. 11,006,876. Exemplary measurement systems and methods used for detecting and modulating the mental state of a user using entertainment selections, e.g., music, film/video, are described in more detail in U.S. patent application Ser. No. 16/835,972, filed Mar. 31, 2020, issued as U.S. Pat. No. 11,006,878. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, issued as U.S. Pat. No. 11,172,869. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

These and other advantages and benefits of the present systems and methods are described more fully herein.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021, published as US2021/0259638A1; U.S. patent application Ser. No. 17/176,309, filed Feb. 16, 2021, published as US2021/0259614A1; U.S. patent application Ser. No. 17/176,460, filed Feb. 16, 2021, issued as U.S. Pat. No. 11,096,620; U.S. patent application Ser. No. 17/176,470, filed Feb. 16, 2021, published as US2021/0259619A1; U.S. patent application Ser. No. 17/176,487, filed Feb. 16, 2021, published as US2021/0259632A1; U.S. patent application Ser. No. 17/176,539, filed Feb. 16, 2021, published as US2021/0259620A1; U.S. patent application Ser. No. 17/176,560, filed Feb. 16, 2021, published as US2021/0259597A1; U.S. patent application Ser. No. 17/176,466, filed Feb. 16, 2021, published as US2021/0263320A1; Han Y. Ban, et al., "Kernel Flow: A High Channel Count Scalable TD-fNIRS System," SPIE Photonics West Conference (Mar. 6, 2021); and Han Y. Ban, et al., "Kernel Flow: a high channel count scalable time-domain functional near-infrared spectroscopy system," Journal of Biomedical Optics (Jan. 18, 2022), which applications and publications are incorporated herein by reference in their entirety.

In some examples, optical measurement operations performed by optical measurement system 100 are associated with a time domain-based optical measurement technique. Example time domain-based optical measurement techniques include, but are not limited to, time-correlated single-photon counting (TCSPC), time domain near infrared spectroscopy (TD-NIRS), time domain diffusive correlation spectroscopy (TD-DCS), and time domain Digital Optical Tomography (TD-DOT).

Optical measurement system 100 (e.g., an optical measurement system that is implemented by a wearable device or other configuration, and that employs a time domain-based (e.g., TD-NIRS) measurement technique) may detect blood oxygenation levels and/or blood volume levels by measuring the change in shape of laser pulses after they have passed through target tissue, e.g., brain, muscle, finger, etc. As used herein, a shape of laser pulses refers to a temporal shape, as represented for example by a histogram generated by a time-to-digital converter (TDC) coupled to an output of a photodetector, as will be described more fully below.

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes, distributed feedback (DFB) lasers, super luminescent diodes (SLDs), light emitting diodes (LEDs), diode-pumped solid-state (DPSS) lasers, super luminescent light emitting diodes (sLEDs), vertical-cavity surface-emitting lasers (VCSELs), titanium sapphire lasers, micro light emitting diode (m LEDs), and/or any other suitable laser or light source configured to emit light in one or more discrete wavelengths or narrow wavelength bands. In some examples, the light emitted by light source 110 is high coherence light (e.g., light that has a coherence length of at least 5 centimeters) at a predetermined center wavelength. In some examples, the light emitted by light source 110 is emitted as a plurality of alternating light pulses of different wavelengths.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 travels via an optical conduit 114 (e.g., a light pipe, a single-mode optical fiber, and/or or a multi-mode optical fiber) to body 102 of a subject. Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by an arrow 120, light emitted by light source 110 enters body 102 at a first location 122 on body 102. Accordingly, a distal end of optical conduit 114 may be positioned at (e.g., right above, in physical contact with, or physically attached to) first location 122 (e.g., to a scalp of the subject). In some examples, the light may emerge from optical conduit 114 and spread out to a certain spot size on body 102 to fall under a predetermined safety limit. At least a portion of the light indicated by arrow 120 may be scattered within body 102.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a light guide, a waveguide, a single-mode optical fiber, and/or a multi-mode optical fiber) is positioned at (e.g., right above, in physical contact with, or physically attached to) output location 126 on body 102. In this manner, optical conduit 116 may collect at least a portion of the scattered light (indicated as light 124) as it exits body 102 at location 126 and carry light 124 to detector 104. Light 124 may pass through one or more lenses and/or other optical elements (not shown) that direct light 124 onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
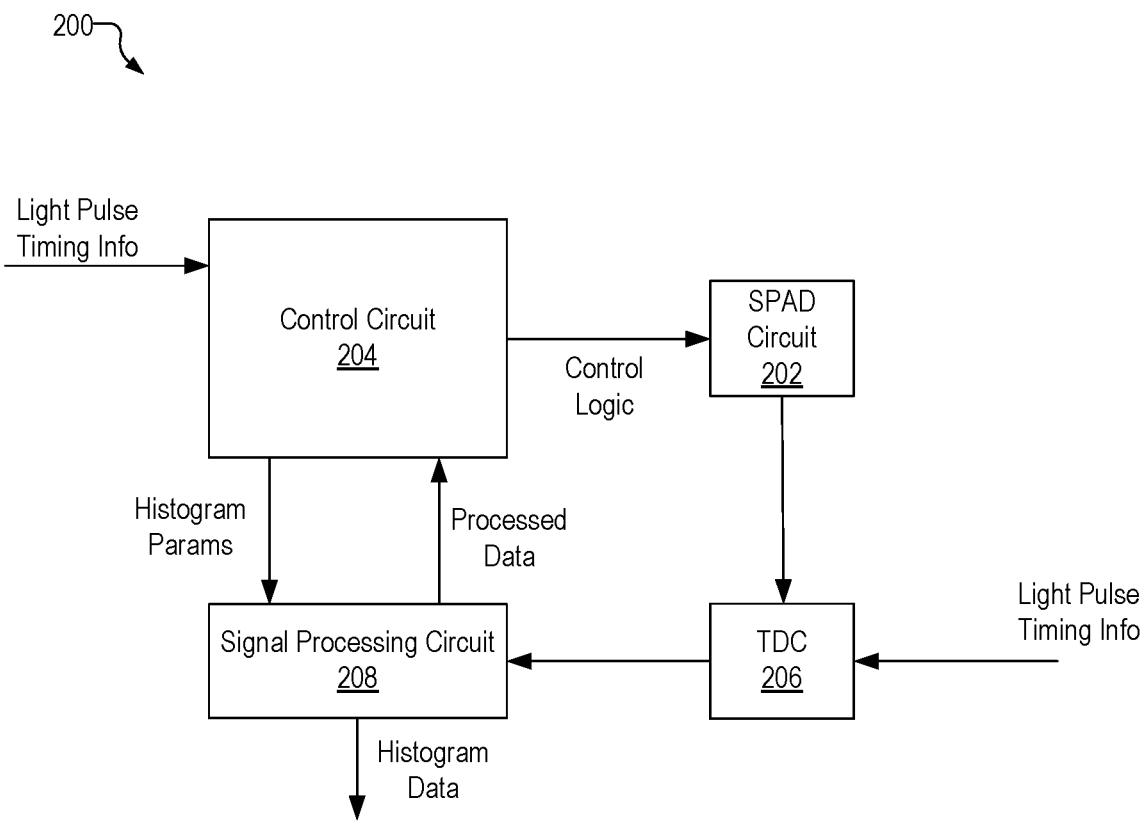
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 may include a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, such as in configurations that implement the systems and methods described herein, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
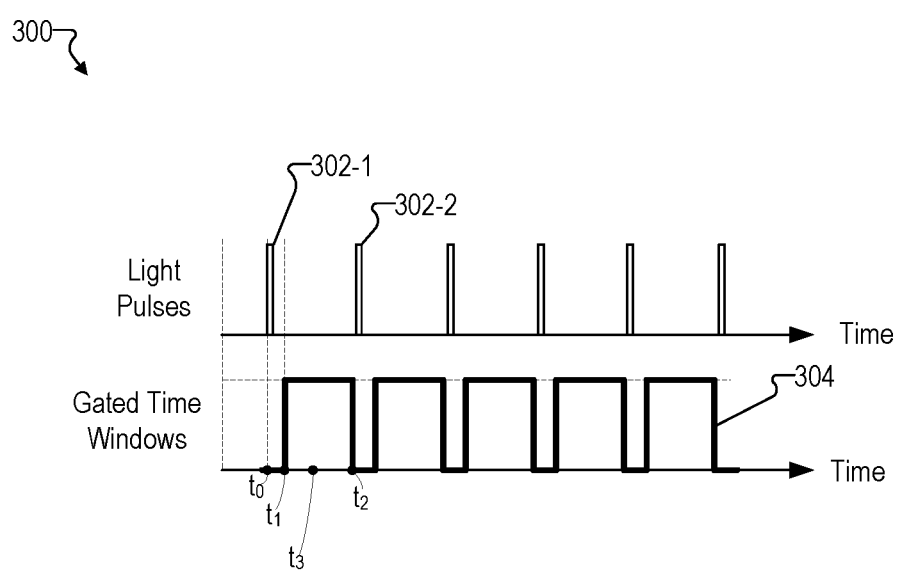
FIG. 3 illustrates an exemplary timing diagram for performing an optical measurement operation using an optical measurement system.

FIG. 3 illustrates an exemplary timing diagram 300 for performing an optical measurement operation using optical measurement system 100. The optical measurement operation may be performed in accordance with a time domain-based technique, such as TD-NIRS. Optical measurement system 100 may be configured to perform the optical measurement operation by directing light pulses (e.g., laser pulses) toward a target within a body (e.g., body 102). The light pulses may be short (e.g., 10-2000 picoseconds (ps))

and repeated at a high frequency (e.g., between 100,000 hertz (Hz) and 100 megahertz (MHz)). The light pulses may be scattered by the target and at least a portion of the scattered light may be detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

Timing diagram 300 shows a sequence of light pulses 302 (e.g., light pulses 302-1 and 302-2) that may be applied to the target (e.g., tissue within a finger of a user, tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. As shown, light pulse 302-1 is applied at a time t0. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time t0, which may minimize photons detected directly from the laser pulse, before the laser pulse reaches the target. However, in some alternative examples, time $t_1$ is set to be equal to time t0.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

Figure 4:
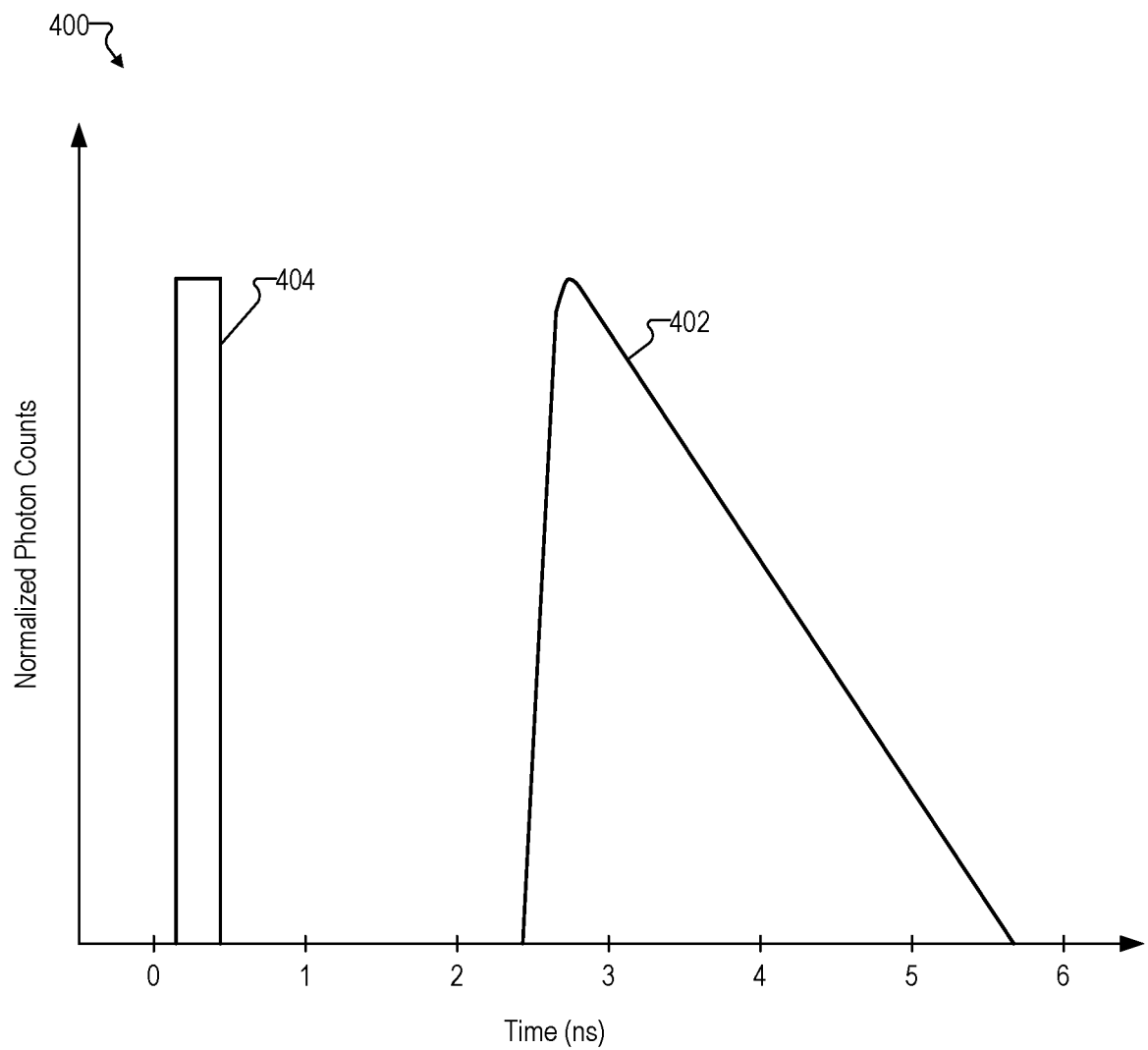
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer biological activity.

Optical measurement system 100 may be implemented by or included in any suitable device. For example, optical measurement system 100 may be included in a non-invasive wearable device (e.g., a headpiece) that a user may wear to perform one or more diagnostic, imaging, analytical, and/or consumer-related operations.

Figure 5:
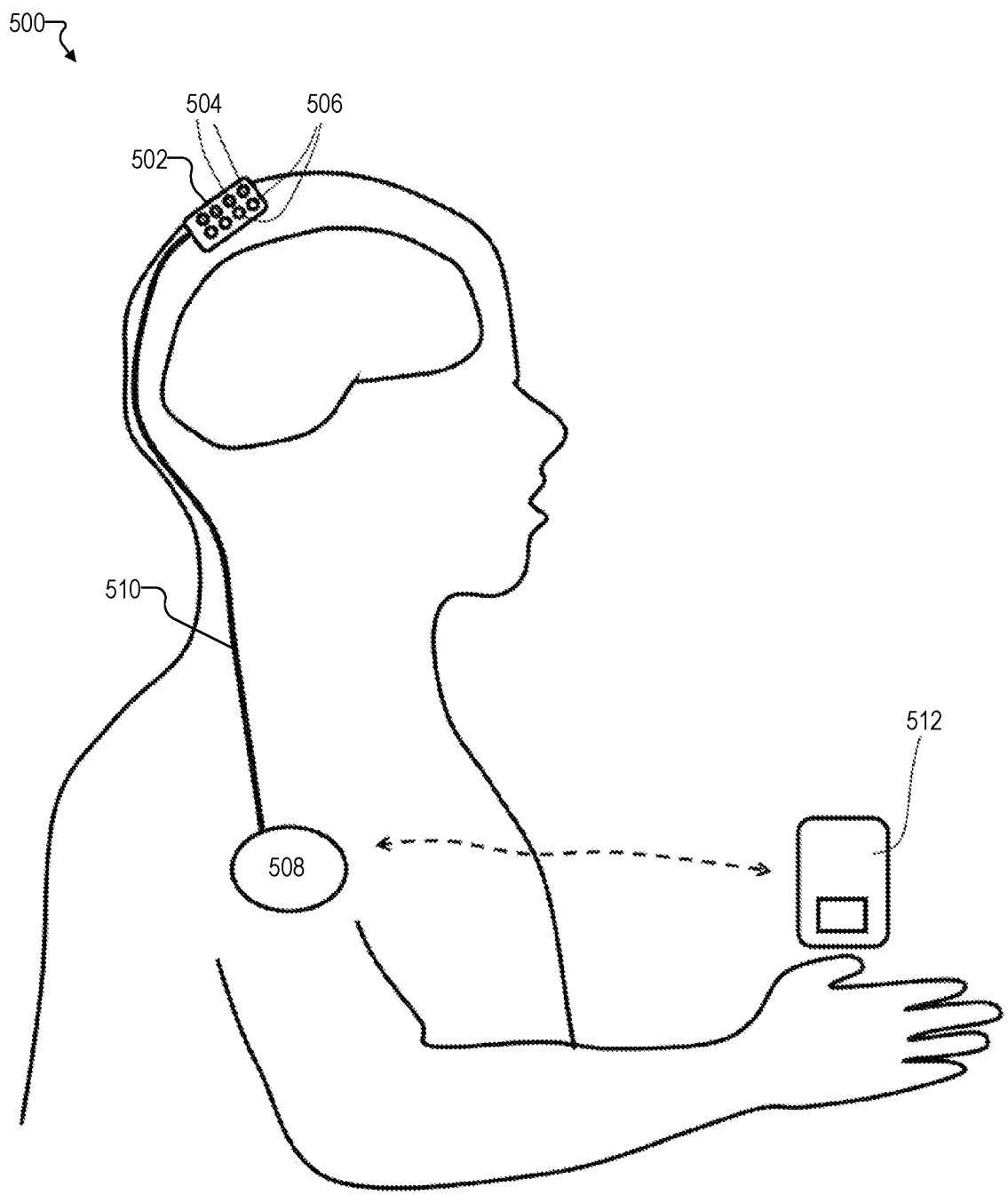
FIG. 5 shows an exemplary non-invasive wearable brain interface system.

To illustrate, FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be a wearable device (e.g., headgear) configured to be worn on a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detectors 504 may be included elsewhere in brain interface system 500. For example, a light source may be included in processor 508 and coupled to head mountable component 502 through optical connections.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Figure 6A:
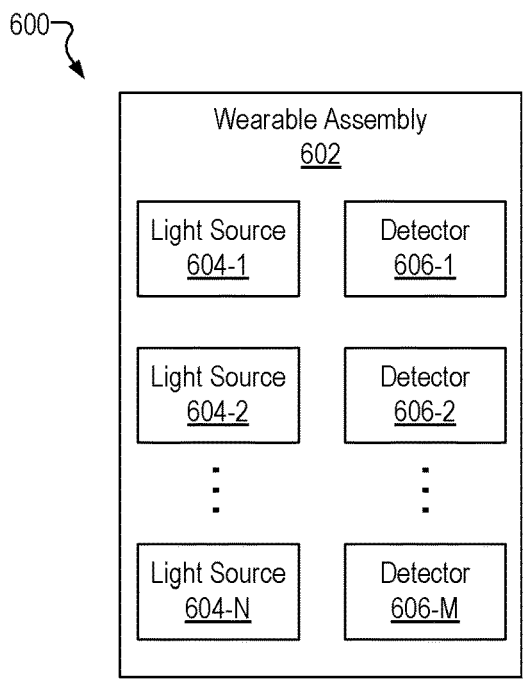
FIGS. 6A and 6B show an exemplary optical measurement system.
Figure 6B:
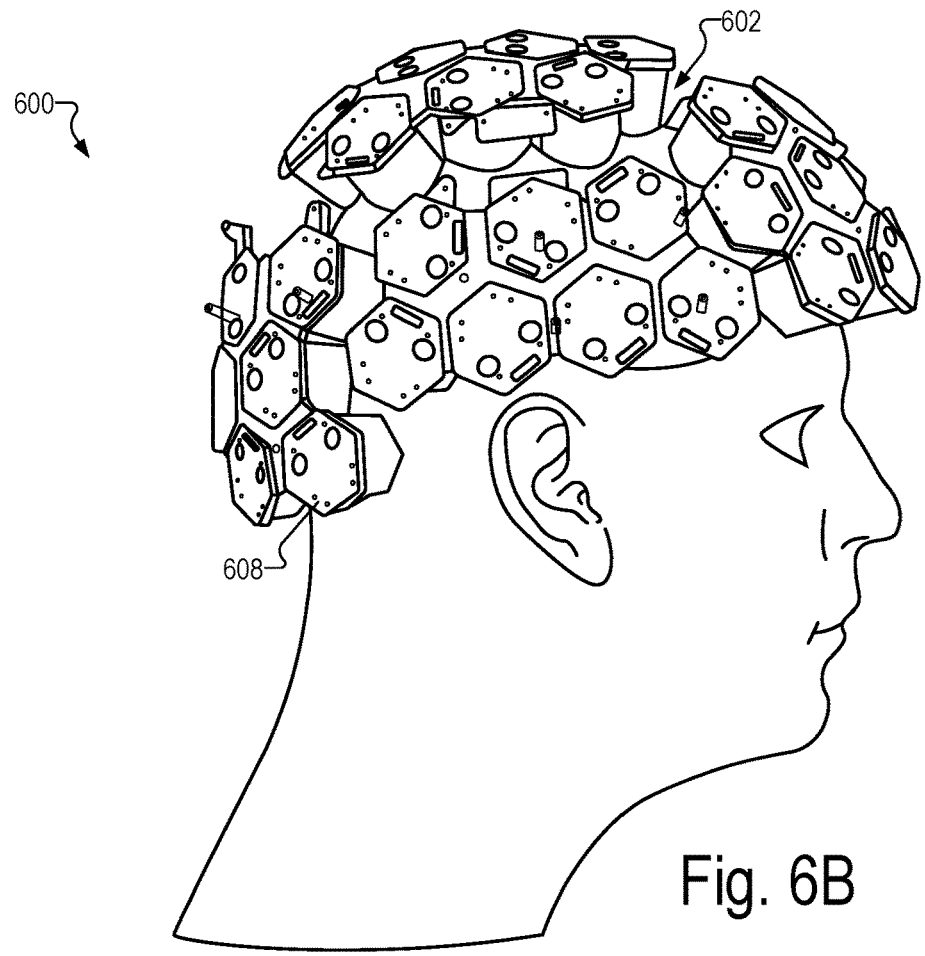

FIGS. 6A and 6B show an exemplary optical measurement system 600 in accordance with the principles described herein. Optical measurement system 600 may be an implementation of optical measurement system 100 and, as shown, includes a wearable assembly 602, which includes N light sources 604 (e.g., light sources 604-1 through 604-N) and M detectors 606 (e.g., detectors 606-1 through 606-M). Optical measurement system 600 may include any of the other components of optical measurement system 100 as may serve a particular implementation. N and M may each be any suitable value (i.e., there may be any number of light sources 604 and detectors 606 included in optical measurement system 600 as may serve a particular implementation).

Light sources 604 are each configured to emit light (e.g., a sequence of light pulses) and may be implemented by any of the light sources described herein. Detectors 606 may each be configured to detect arrival times for photons of the light emitted by one or more light sources 604 after the light is scattered by the target. For example, a detector 606 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector).

Wearable assembly 602 may be implemented by any of the wearable devices, modular assemblies, and/or wearable units described herein. For example, as shown in FIG. 6B, wearable assembly 602 may be implemented by a wearable device (e.g., headgear) configured to be worn on a user's head. The TD-NIRS optical measurement system 600 shown in FIG. 6B may include a plurality of modules 608 arranged in a helmet design. In some examples, modules 608 may be organized on each side of the head, covering the frontal, parietal, temporal, and occipital cortices. Wearable assembly 602 may additionally or alternatively be configured to be worn on any other part of a user's body.

Optical measurement system 600 may be modular in that one or more components of optical measurement system 600 may be removed, changed out, or otherwise modified as may serve a particular implementation. As such, optical measurement system 600 may be configured to conform to three-dimensional surface geometries, such as a user's head, e.g., see FIG. 6B. Exemplary modular optical measurement systems are described in more detail in U.S. patent application Ser. No. 17/176,460, filed Feb. 16, 2021, issued as U.S. Pat. No. 11,096,620; U.S. patent application Ser. No. 17/176,470, filed Feb. 16, 2021, published as US2021/0259619A1; U.S. patent application Ser. No. 17/176,487, filed Feb. 16, 2021, published as US2021/0259632A1; U.S. patent application Ser. No. 17/176,539, filed Feb. 16, 2021, published as US2021/0259620A1; U.S. patent application Ser. No. 17/176,560, filed Feb. 16, 2021, published as US2021/0259597A1; and U.S. patent application Ser. No. 17/176,466, filed Feb. 16, 2021, published as US2021/0263320A1; which applications and publications are incorporated herein by reference in their respective entireties.

Figure 7:
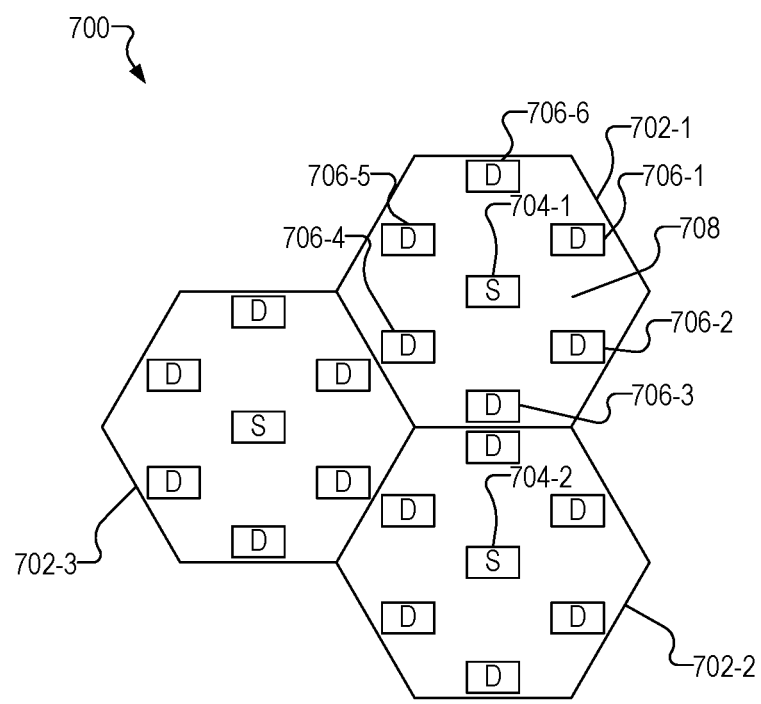
FIG. 7 shows an illustrative modular assembly.

FIG. 7 shows an illustrative modular assembly 700 that may implement optical measurement system 600. Modular assembly 700 is illustrative of the many different implementations of optical measurement system 600 that may be realized in accordance with the principles described herein.

As shown, modular assembly 700 includes a plurality of modules 702 (e.g., modules 702-1 through 702-3). While three modules 702 are shown to be included in modular assembly 700, in alternative configurations, any number of modules 702 (e.g., a single module unit up to sixteen or more module units) may be included in modular assembly 700.

Each module unit 702 includes a light source (e.g., light source 704-1 of module 702-1 and light source 704-2 of module 702-2) and a plurality of detectors (e.g., detectors 706-1 through 706-6 of module 702-1). In the particular implementation shown in FIG. 7, each module unit 702 includes a single light source and six detectors. Each light source is labeled "S" and each detector is labeled "D".

Each light source depicted in FIG. 7 may be implemented by one or more light sources similar to light source 110 and may be configured to emit light directed at a target (e.g., the brain).

Each light source depicted in FIG. 7 may be located at a center region of a surface of the light source's corresponding module. For example, light source 704-1 is located at a center region of a surface 708 of module 702-1. In alternative implementations, a light source of a module may be located away from a center region of the module.

Each detector depicted in FIG. 7 may implement or be similar to detector 104 and may include a plurality of photodetectors (e.g., SPADs) as well as other circuitry (e.g., TDCs), and may be configured to detect arrival times for photons of the light emitted by one or more light sources after the light is scattered by the target.

The detectors of a module may be distributed around the light source of the module. For example, detectors 706 of module 702-1 are distributed around light source 704-1 on surface 708 of module 702-1. In this configuration, detectors 706 may be configured to detect photon arrival times for photons included in light pulses emitted by light source 704-1. In some examples, one or more detectors 706 may be close enough to other light sources to detect photon arrival times for photons included in light pulses emitted by the other light sources. For example, because detector 706-3 is adjacent to module 702-2, detector 706-3 may be configured to detect photon arrival times for photons included in light pulses emitted by light source 704-2 (in addition to detecting photon arrival times for photons included in light pulses emitted by light source 704-1).

In some examples, the detectors of a module may all be equidistant from the light source of the same module. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light source, e.g., light emitter, and the detector allows subsequent processing of the detected signals to infer spatial (e.g., depth localization, inverse modeling) information about the detected signals. Detectors of a module may be alternatively disposed on the module as may serve a particular implementation.

Figure 8A:
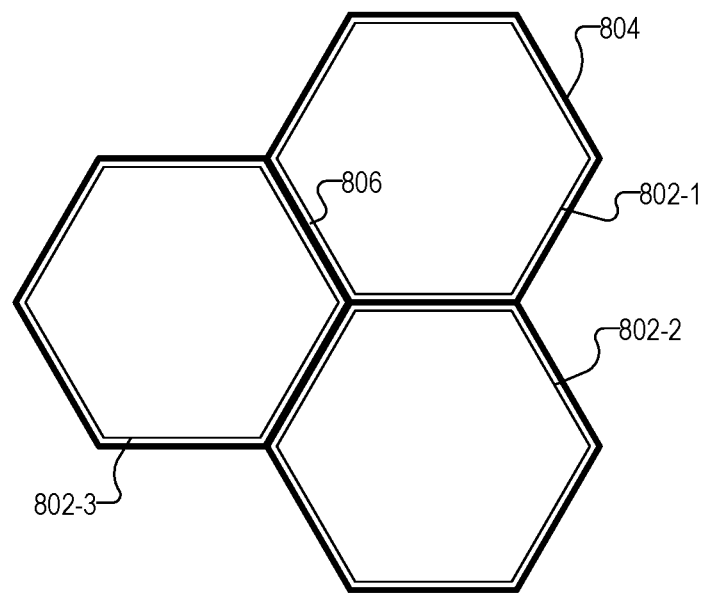
FIGS. 8A-8B show an exemplary implementation of the modular assembly of FIG. 7.
Figure 8B:
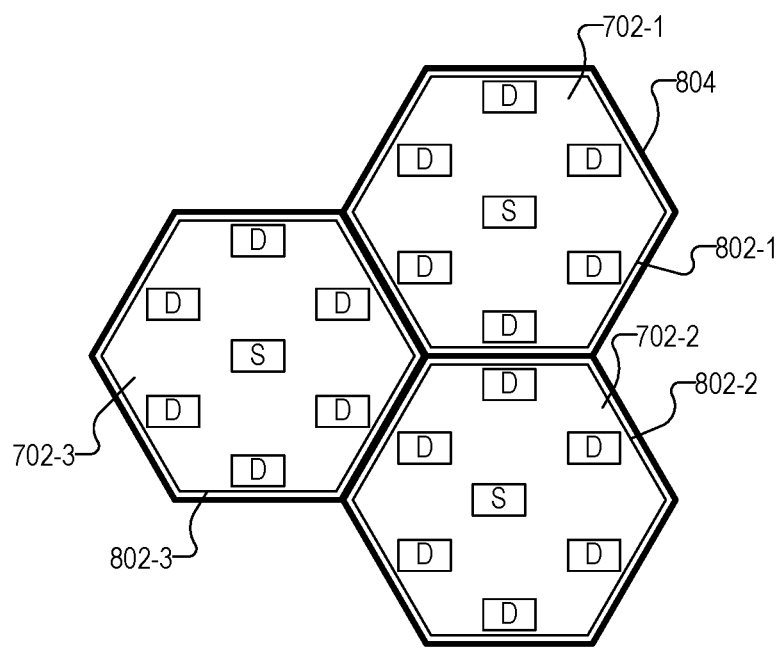

In FIG. 7, modules 702 are shown to be adjacent to and touching one another. Modules 702 may alternatively be spaced apart from one another. For example, FIGS. 8A-8B show an exemplary implementation of modular assembly 700 in which modules 702 are configured to be inserted into individual slots 802 (e.g., slots 802-1 through 802-3, also referred to as cutouts) of a wearable assembly 804. In particular, FIG. 8A shows the individual slots 802 of the wearable assembly 804 before modules 702 have been inserted into respective slots 802, and FIG. 8B shows wearable assembly 804 with individual modules 702 inserted into respective individual slots 802.

Wearable assembly 804 may implement wearable assembly 602 and may be configured as headgear and/or any other type of device configured to be worn by a user. See for example FIG. 6B.

As shown in FIG. 8A, each slot 802 is surrounded by a wall (e.g., wall 806) such that when modules 702 are inserted into their respective individual slots 802, the walls physically separate modules 702 one from another. In alternative embodiments, a module (e.g., module 702-1) may be in at least partial physical contact with a neighboring module (e.g., module 702-2).

Each of the modules described herein may be inserted into appropriately shaped slots or cutouts of a wearable assembly, as described in connection with FIGS. 8A-8B. However, for ease of explanation, such wearable assemblies are not shown in the figures.

As shown in FIGS. 7 and 8B, modules 702 may have a hexagonal shape. Modules 702 may alternatively have any other suitable geometry (e.g., in the shape of a pentagon, octagon, square, rectangular, circular, triangular, free-form, etc.).

Figure 9:
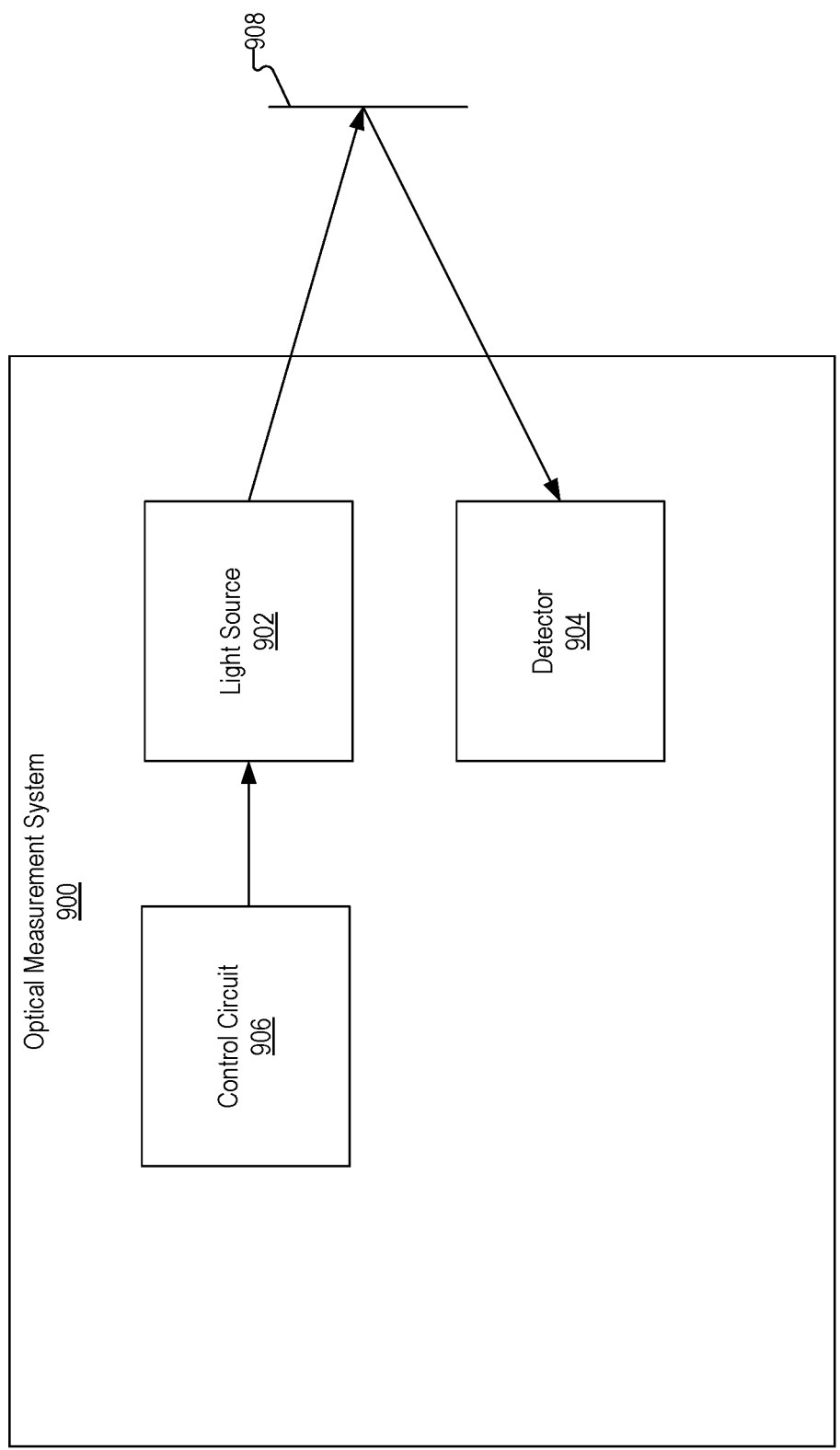
FIG. 9 shows an exemplary optical measurement system.

FIG. 9 shows an exemplary optical measurement system 900 that may be similar to and/or implement any of the optical measurement systems described herein. Optical measurement system 900 includes a light source 902 (e.g., an implementation of light source 110), a detector 904 (e.g., an implementation of detector 104), and a control circuit 906. Control circuit 906 may be configured to drive light source 902 (e.g., by selectively providing power to light source 902). Control circuit 906 may be implemented by controller 112 and/or any other suitable circuit, controller, computing and/or processing device. Exemplary implementations of control circuit 906 are described herein.

Light source 902 may be configured to direct light (e.g., light pulses) at a target 908 (e.g., body 102). Detector 904 may include a plurality of photodetectors configured to detect photons of the light emitted by light source 902 after the light is scattered by target 908. Detector 904 may detect arrival times of the photons at detector 904 and provide output data to a processing unit (e.g., an implementation of processor 108, not shown) indicating the arrival times. The processing unit may generate, based on the arrival times, histogram data (e.g., TPSF 402) associated with target 908. The processing unit may determine, based on the histogram data, an optical property associated with target 908.

Control circuit 906 may be configured to drive light source 902 in any suitable manner. For instance, light source 902 may be implemented using a laser diode in a gain switching mode and configured to generate narrow optical pulses (e.g., on the order of 1 nanosecond (ns), 100 picoseconds (ps) or less, etc.) at a high repetition rate (e.g., on the order of 1 megahertz (MHz), 10 MHz or higher, etc.). Control circuit 906 may output a current pulse configured to optimize efficiency in driving such a laser diode. For example, a current pulse may include a rise phase, during which electrons are injected to build a carrier density up to a threshold density. Once the threshold density is met, population inversion may be achieved and the laser diode may begin to emit a light pulse. As the emission begins to consume the carrier, a maximum current of the current pulse may be provided to the laser diode (e.g., at a time between the carrier density reaching the threshold density and a peak emission of the light pulse). At the peak emission of the light pulse, the current pulse may be terminated quickly to restrain a secondary optical oscillation. Thus, the current pulse may include a decline phase, when the current pulse is taken from a maximum output to zero (or other sufficiently low output value). The decline phase may have a duration that is within a threshold percentage (e.g., 20%, 10%, or any suitable threshold percentage) of a total pulse duration.

In some examples, under various assumptions and with particular characteristics of the laser diode, an equation for an optimal current pulse may be determined. For instance, an optimal current pulse for some light sources may be defined by an optimal current pulse equation such as $$I(t) = \frac{eVN_{th}}{\tau_N \sinh(T/\tau_N)} \exp(t/\tau_N),$$

where e is the elementary charge constant, V is a volume of an active region of the light source, $N_{th}$ is a lasing threshold carrier density of the light source, T is the total pulse duration, and $\tau_N$ is a growth rate constant of the light source.

Figure 10:
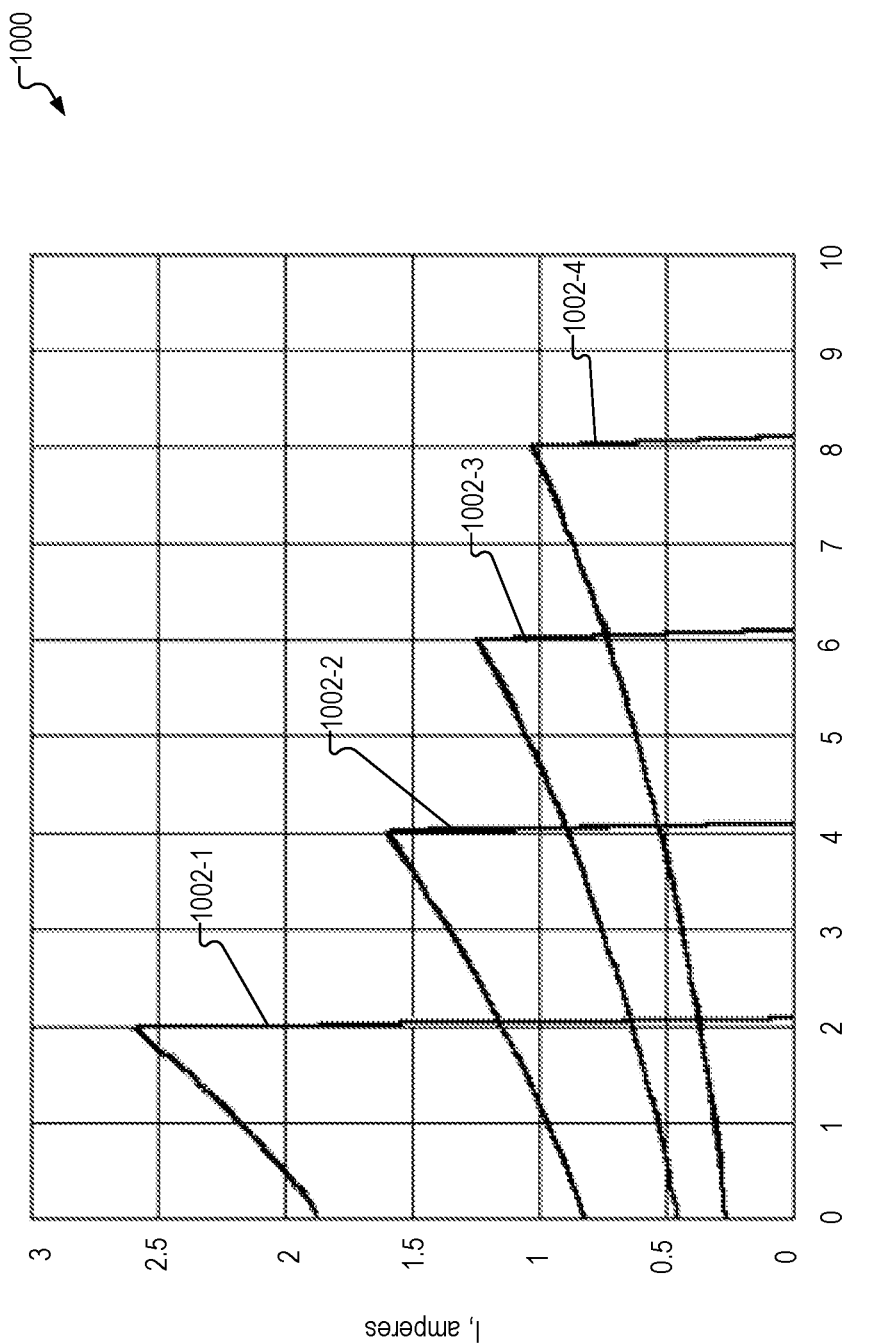
FIG. 10 shows exemplary current pulses.

FIG. 10 illustrates an exemplary graph 1000 that shows example current pulses defined by such an optimal current pulse equation. As shown, graph 1000 includes four current pulses 1002 (e.g., pulses 1002-1 through 1002-4) that have different total pulse durations (T). Each current pulse 1002 is shown with values of a current (I) in amperes (A) versus a time (t) in nanoseconds (ns). Each current pulse 1002 may depict an optimal current pulse for driving a laser diode (e.g., an implementation of light source 902) to output narrow optical pulses with a high repetition rate. As shown, current pulses 1002 may share some characteristics, such as a linear (e.g., an exponential) rise, a non-zero starting current value, and a sharp decline (e.g., having a duration that is within a threshold percentage of the total pulse duration). While graph 1000 shows current pulses 1002 with four particular pulse durations, any suitable total pulse duration may be used.

Any suitable implementation of a control circuit (e.g., control circuit 906) that outputs a current pulse similar to any of the current pulses depicted in graph 1000 and/or defined by the optimal current pulse equation may be used. For instance, control circuit 906 may include any implementation that outputs a current pulse that is within a threshold variance from an optimal pulse defined by the optimal current pulse equation. The variance may be measured in any suitable manner and the threshold may be any suitable threshold.

Figure 11:
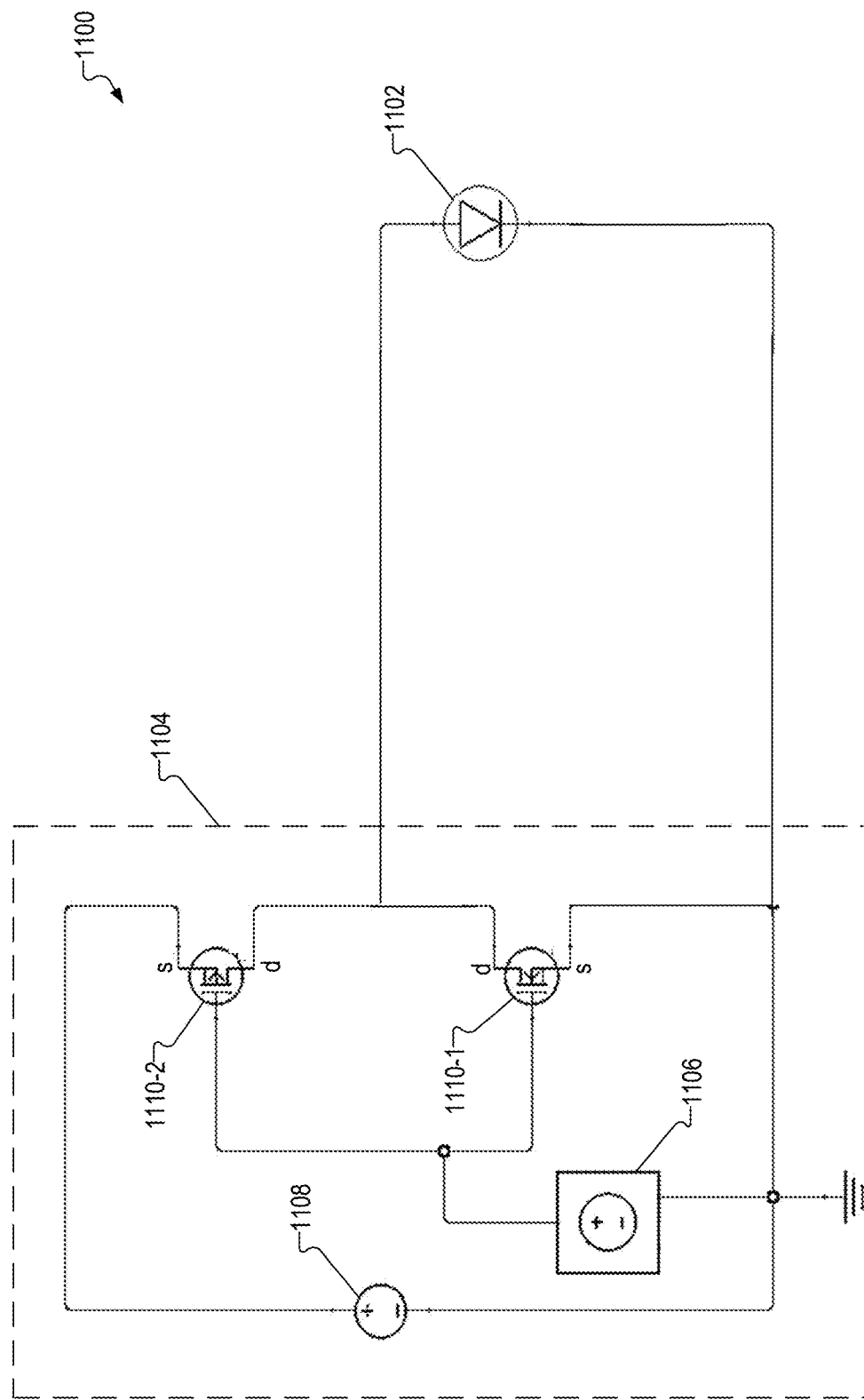
FIGS. 11-15 show exemplary control circuits.

FIG. 11 shows an exemplary configuration 1100 of a control circuit (e.g., control circuit 906) configured to drive a laser diode 1102 (e.g., an implementation of light source 902). As shown, configuration 1100 includes a driver circuit 1104 coupled to laser diode 1102. Driver circuit 1104 may be implemented as a push-pull driver, including a rectangular pulse voltage source 1106 configured to output rectangular pulses that range from 0 volts (V) to a voltage determined by a power supply 1108. Driver circuit 1104 further includes two complementary transistors 1110, a pull-up transistor 1110-1 and a pull-down transistor 1110-2.

Transistors 1110 may be implemented using any suitable transistor, such as a bipolar junction transistor (BJT). Control circuit 906 may be configured so that pull-up transistor 1110-1 is turned on during a rise of a current pulse generated by driver circuit 1104 so that the current is applied through pull-up transistor 1110-1 to charge laser diode 1102. During a decline of the current pulse, pull-down transistor 1110-2 may be turned on (and pull-up transistor 1110-1 turned off) so that laser diode 1102 is shorted through pull-down transistor 1110-2.

Driver circuit 1104 may further include various components so that a variance between a current pulse generated by driver circuit 1104 and an optimal current pulse shape (e.g., a current pulse defined by an optimal current pulse equation) may be minimized.

Figure 12:
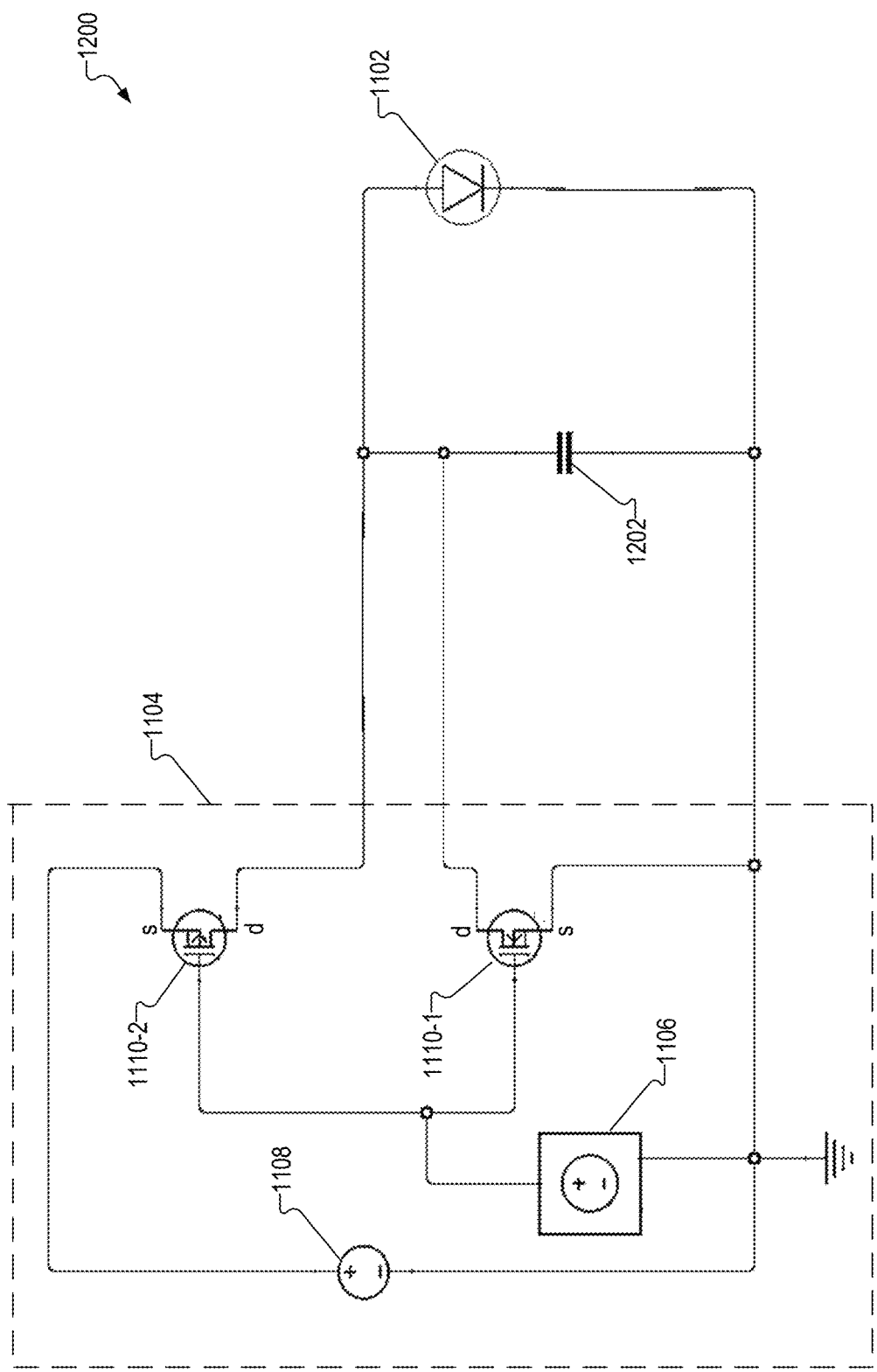

For example, FIG. 12 shows another exemplary configuration 1200 of control circuit 906. Similar to configuration 1100, configuration 1200 includes laser diode 1102 and driver circuit 1104, which includes rectangular pulse voltage source 1106, power supply 1108, and transistors 1110. In configuration 1200, control circuit 906 further includes a capacitor 1202 coupled in parallel with laser diode 1102.

Capacitor 1202 coupled in parallel with laser diode 1102 may allow a shape of a current pulse for driving laser diode 1102 to vary from an optimal current pulse shape less than a similar control circuit that does not include capacitor 1202. For instance, without capacitor 1202, the rise of the current pulse may be more linear than with capacitor 1202.

Additionally, configuration 1200 may be configured to achieve a sharp decline in the shape of the current pulse, for instance, by coupling pull-up transistor 1110-1 via a path with a higher inductance than pull-down transistor 1110-2. Such a higher inductance path may be implemented in any suitable manner, such as by including an inductor (not shown) and/or by using a longer path for pull-up transistor 1110-1 than for pull-down transistor 1110-2 (e.g., using a longer trace on a printed circuit board (PCB)).

Figure 13:
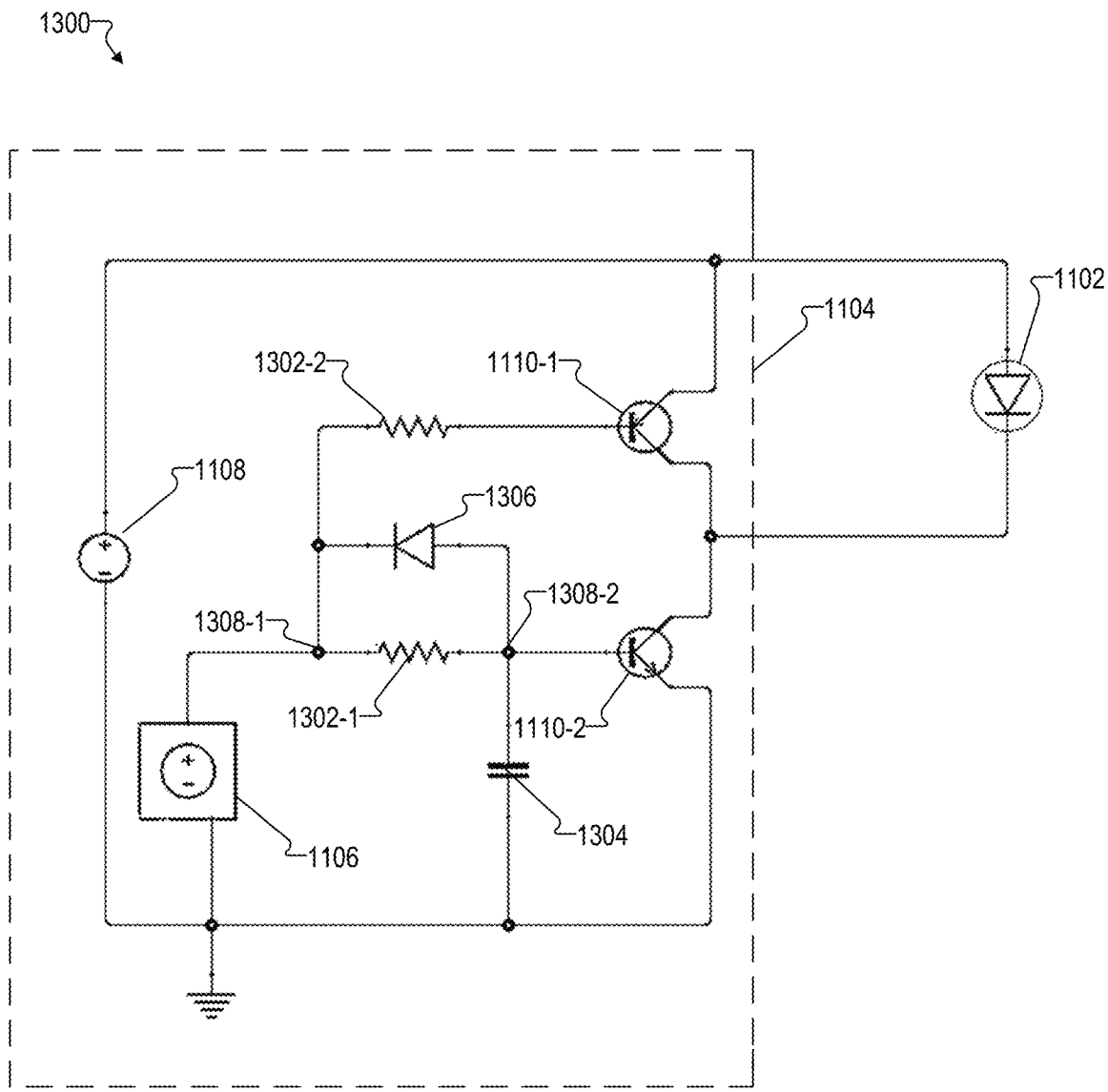

FIG. 13 shows another exemplary configuration 1300 of control circuit 906. Similar to configuration 1100, configuration 1300 includes laser diode 1102 and driver circuit 1104, which includes rectangular pulse voltage source 1106, power supply 1108, and transistors 1110. In configuration 1300, driver circuit 1104 may further include resistors 1302 (e.g., resistor 1302-1 and 1302-2), a capacitor 1304, and a diode 1306.

In an example operation of configuration 1300, during a rise of a current pulse output by driver circuit 1104, voltage at a first node 1308-1 may increase and become equal to a voltage of power supply 1108. At this point, voltage at a second node 1308-2 may start to rise due to resistor 1302-1 and capacitor 1304. The rising voltage at node 1308-2 may be approximately linear at short time scales. This may result in the current output to laser diode 1102 to rise exponentially (e.g., due to the Ebers-Moll equation, which may model the current output by a BJT transistor in active mode).

Once laser diode 1102 has emitted a light pulse, voltage at node 1308-1 may be driven to 0 V and pull-down transistor 1110-2 turned on. Meanwhile, a base of pull-up transistor 1110-1 may be driven to 0 V through diode 1306 and turned off. Diode 1306 may be configured so that a forward voltage drop is lower than a base-emitted threshold voltage of pull-up transistor 1110-1. As a result, a voltage variance at node 1308-2 may be between the forward voltage of diode 1306 and slightly above the base-emitted threshold voltage of pull-up transistor 1110-1. Resistor 1302-2 may be configured to balance delays between turning on pull-down transistor 1110-2 and turning off pull-up transistor 1110-1 to minimize a shoot-through current. The resulting current pulse output by driver circuit 1104 may approximate an optimal current pulse shape.

Figure 14:
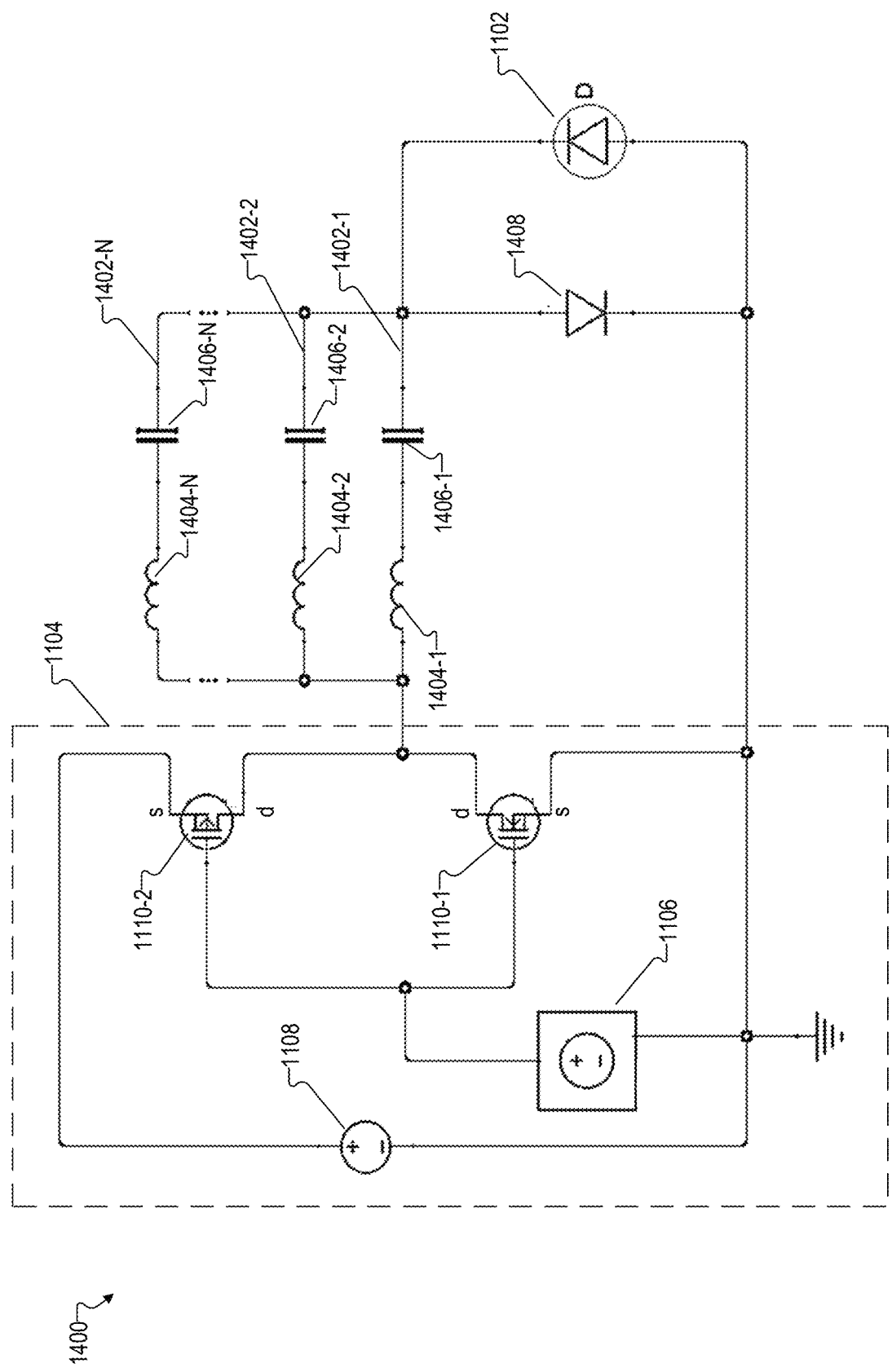

FIG. 14 shows another exemplary configuration 1400 of control circuit 906. Similar to configuration 1100, configuration 1400 includes laser diode 1102 and driver circuit 1104, which includes rectangular pulse voltage source 1106, power supply 1108, and transistors 1110. In configuration 1400, control circuit 906 further includes a plurality of resonant circuits 1402 (e.g., resonant circuits 1402-1 through 1402-N) coupled in parallel. Each resonant circuit 1402 includes an inductor 1404 (e.g., inductors 1404-1 through 1404-N) and a capacitor 1406 (e.g., capacitors 1406-1 through 1406-N). Control circuit 906 may further include a reverse diode 1408.

Resonant circuits 1402 may be configured to each add a sine wave current to a combined current pulse, so that the current pulse shape is defined by superposed sine wave currents of resonant circuits 1402. For example, with a plurality of resonant circuits 1402 coupled to laser diode 1102, the combined current may be approximated using an equation such as $$I(t) = -V_0 \sum_i \frac{\sin(t/\sqrt{L_i C_i})}{\sqrt{L_i C_i}},$$

where $V_0$ is an initial voltage of capacitors 1406. Thus, based on a selection of inductors 1404 and capacitors 1406, the current pulse shape may be configured to be sufficiently close (e.g., within a threshold variance) to an optimal current pulse shape. Further, the current pulse shape based on superposed sine wave currents from resonant circuits 1402 may be configured to include a steeper decline than a sinusoidal current from a single resonant circuit 1402.

Reverse diode 1408 may be configured to be coupled parallel to laser diode 1102. In some examples, laser diode 1102 may be connected in reverse, with an anode coupled to ground, and reverse diode 1408 connected antiparallel to laser diode 1102. Reverse diode 1408 may be configured to charge capacitors 1406 of resonant circuits 1402.

In an example operation of configuration 1400, pull-up transistor 1110-1 may turn on and capacitors 1406 may be charged by reverse diode 1408. Once capacitors 1406 are charged, pull-up transistor 1110-1 may be turned off and pull-down transistor 1110-2 turned on. As pull-down transistor 1110-2 may be bidirectionally conductive, a direction of current through pull-down transistor 1110-2 may be from drain to source of pull-down transistor 1110-2, through laser diode 1102 and resonant circuits 1402. As control circuit 906 is capacitively coupled, control circuit 906 may turn off naturally so that a precise timing of a decline of the current pulse is obviated.

In some examples, control circuit 906 may include three resonant circuits 1402, as additional resonant circuits beyond three may result in circuit paths with lengths that add too much inductance to the resonant circuit. In other examples, control circuit 906 may include two resonant circuits 1402 or four or more resonant circuits 1402.

Figure 15:
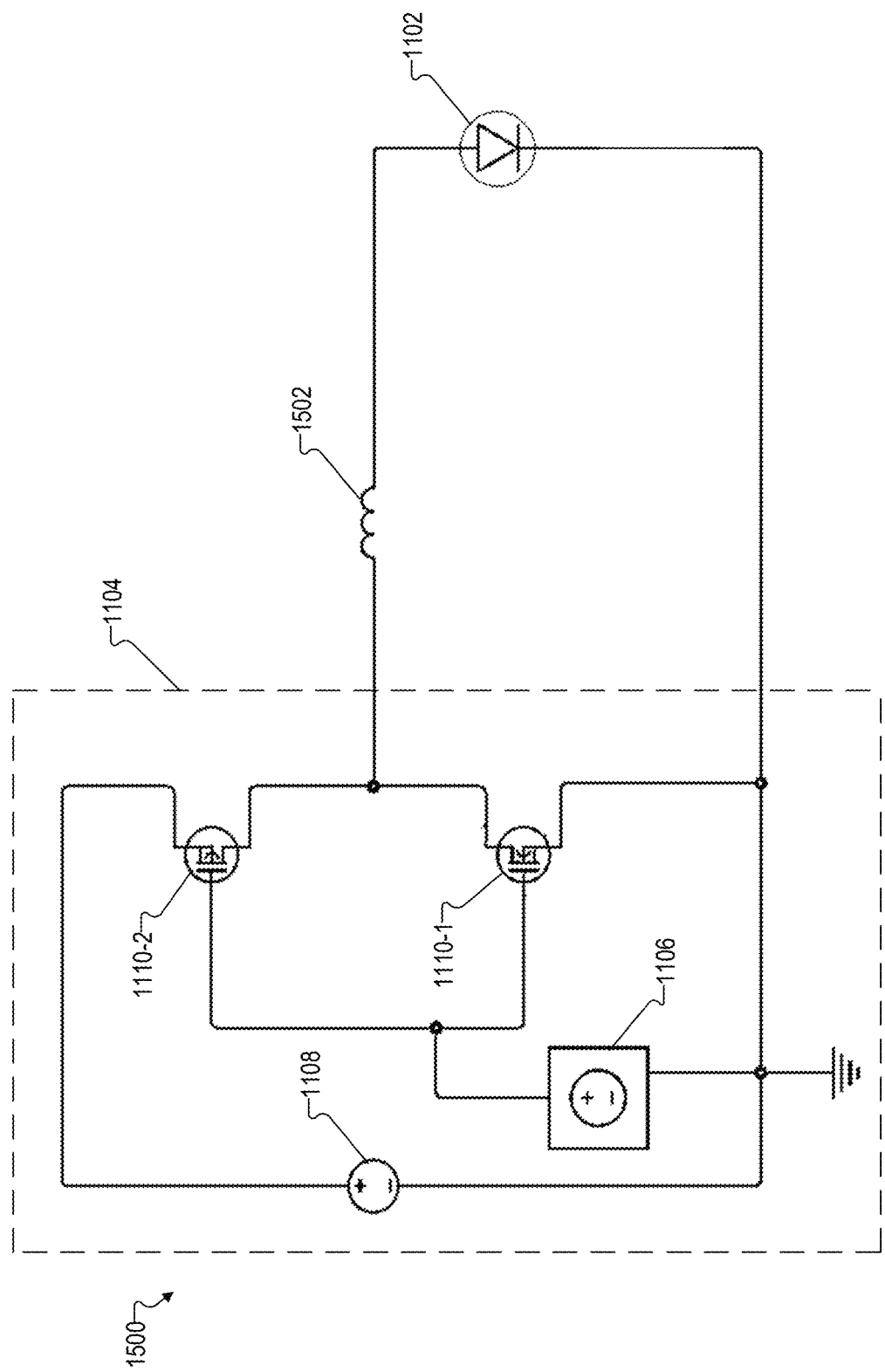

FIG. 15 shows another exemplary configuration 1500 of control circuit 906. Similar to configuration 1100, configuration 1500 includes laser diode 1102 and driver circuit 1104, which includes rectangular pulse voltage source 1106, power supply 1108, and transistors 1110. In configuration 1500, control circuit 906 further includes a nonlinear inductor 1502.

When magnetic flux in nonlinear inductor 1502 approaches a saturation limit of nonlinear inductor 1502, current output may start rising quickly, which may be used to generate an approximately exponential rise in the output current. In an example operation of configuration 1500, transistor 1110-1 may turn on, coupling nonlinear inductor 1502 to power supply 1108. The current output by control circuit 906 may then be defined by $$\frac{dI}{dt} = \frac{V}{L(I) + L_{diode}},$$

where I is current, t is time, V is a voltage of power supply 1108, L is an inductance of nonlinear inductor 1502, and $L_{diode}$ is a parasitic inductance of laser diode 1102. Thus, the presence of nonlinear inductor 1502 may allow a current pulse generated by control circuit 906 to approximate an optimal current pulse shape.

In some examples, components of the example configurations described herein may be combined. As one example, nonlinear inductor 1502 may be included in configuration 1200. Other examples may include any other suitable combination of components and configurations.

Figure 16:
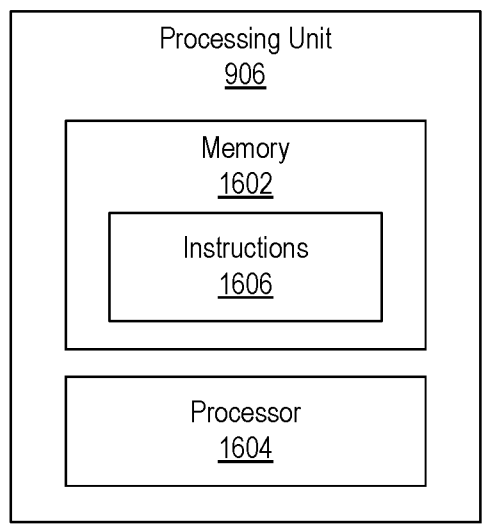
FIG. 16 illustrates an exemplary implementation of a processing unit.

FIG. 16 illustrates an exemplary implementation of a processing unit (e.g., processor 108) that includes a memory 1602 and a processor 1604 configured to be selectively and communicatively coupled to one another. In some examples, memory 1602 and processor 1604 may be distributed between multiple devices and/or multiple locations as may serve a particular implementation.

Memory 1602 may be implemented by any suitable non-transitory computer-readable medium and/or non-transitory processor-readable medium, such as any combination of non-volatile storage media and/or volatile storage media. Exemplary non-volatile storage media include, but are not limited to, read-only memory, flash memory, a solid-state drive, a magnetic storage device (e.g., a hard drive), ferroelectric random-access memory ("RAM"), and an optical disc. Exemplary volatile storage media include, but are not limited to, RAM (e.g., dynamic RAM).

Memory 1602 may maintain (e.g., store) executable data used by processor 1604 to perform one or more of the operations described herein. For example, memory 1602 may store instructions 1606 that may be executed by processor 1604 to perform any of the operations described herein. Instructions 1606 may be implemented by any suitable application, program (e.g., sound processing program), software, code, and/or other executable data instance. Memory 1602 may also maintain any data received, generated, managed, used, and/or transmitted by processor 1604.

Processor 1604 may be configured to perform (e.g., execute instructions 1606 stored in memory 1602 to perform) various operations described herein. For example, processor 1604 may be configured to perform any of the operations described herein as being performed by the processing unit.

In some examples, the processing unit may be included in the same wearable system (e.g., a head-mountable component) that includes a light source (e.g., light source 902) and a detector (e.g., detector 904). Alternatively, the processing unit is not included in the same wearable system that includes light source 902 and detector 904.

To illustrate, the processing unit may be included in a wearable device separate from a head-mountable component that includes light source 902 and detector 904. For example, the processing unit may be included in a wearable device configured to be worn off the head while the head-mountable component is worn on the head. In these examples, one or more communication interfaces (e.g., cables, wireless interfaces, etc.) may be used to facilitate communication between the head-mountable component and the separate wearable device.

Additionally or alternatively, the processing unit may be remote from the user (i.e., not worn by the user). For example, the processing unit may be implemented by a stand-alone computing device communicatively coupled the head-mountable component by way of one or more communication interfaces (e.g., cables, wireless interfaces, etc.).

FIGS. 17-22 illustrate embodiments of a wearable device 1700 that includes elements of the optical detection systems described herein. In particular, the wearable devices 1700 shown in FIGS. 17-22 include a plurality of modules 1702, similar to the module units described herein. For example, each module 1702 may include a light source (e.g., light source 704-1) and a plurality of detectors (e.g., detectors 706-1 through 706-6). The wearable devices 1700 may each also include a controller (e.g., controller 112) and a processor (e.g., processor 108) and/or be communicatively connected to a controller and processor. In general, wearable device 1700 may be implemented by any suitable headgear and/or clothing article configured to be worn by a user. The headgear and/or clothing article may include batteries, cables, and/or other peripherals for the components of the optical measurement systems described herein.

Figure 17:
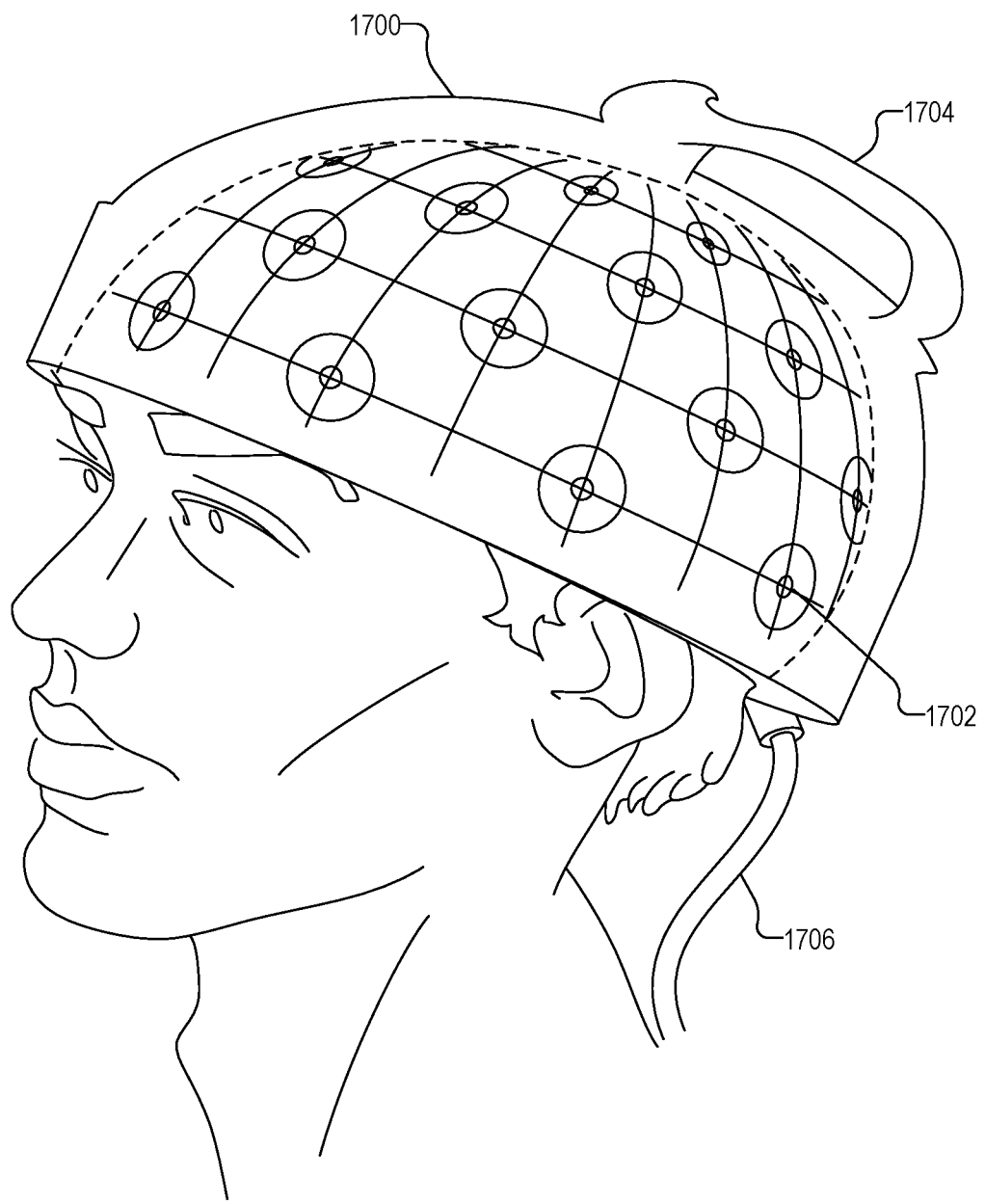
FIGS. 17-22 illustrate embodiments of a wearable device that includes elements of the optical detection systems described herein.
Figure 18:
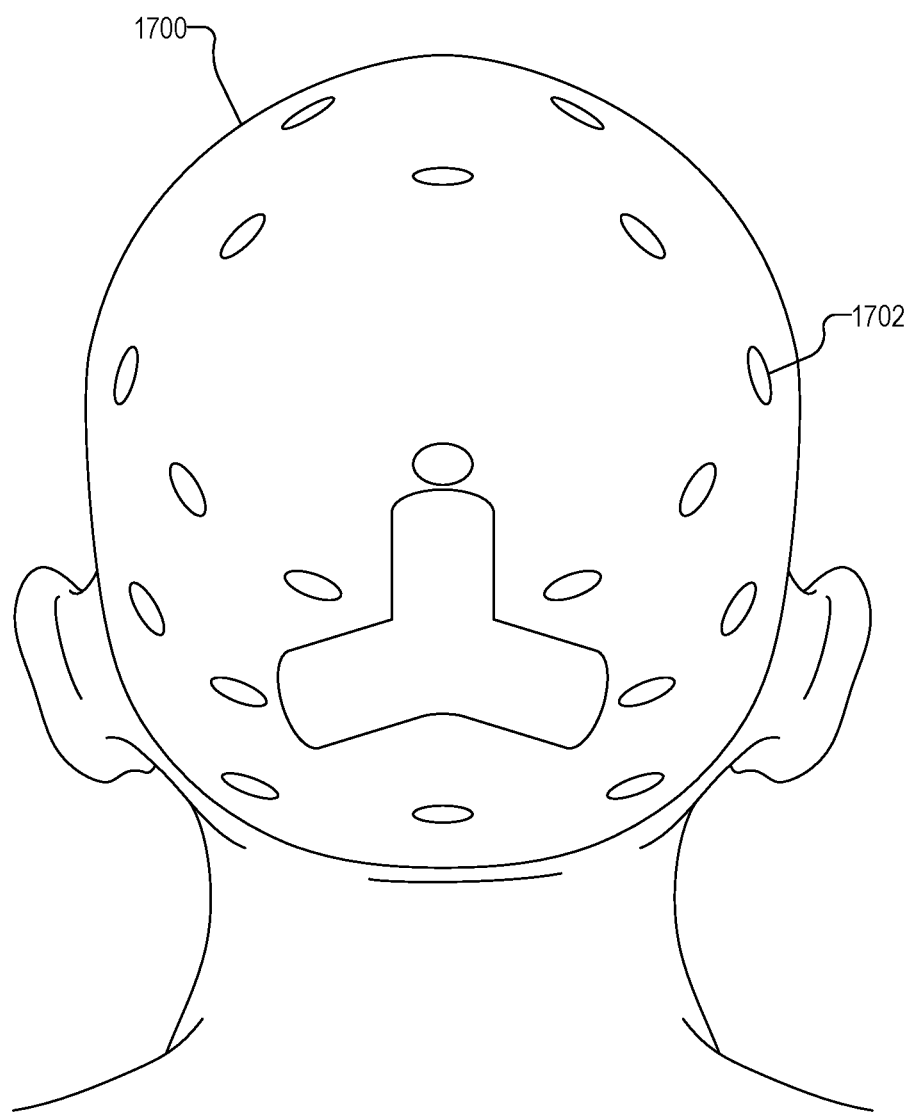
Figure 19:
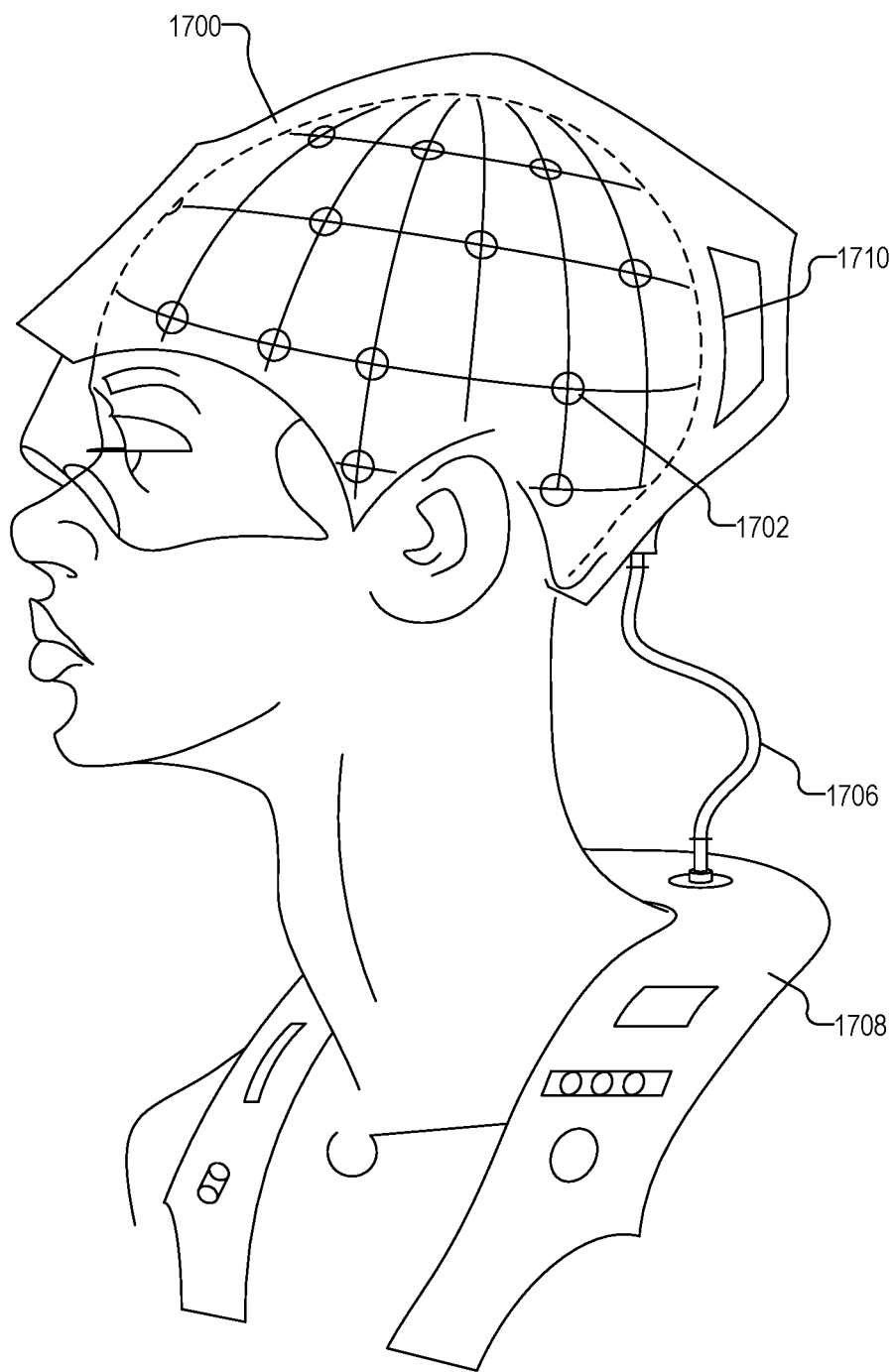

FIG. 17 illustrates an embodiment of a wearable device 1700 in the form of a helmet with a handle 1704. In some embodiments handle 1704 may be optional. A cable 1706 extends from the wearable device 1700 for attachment to a battery or hub (with components such as a processor or the like). FIG. 18 illustrates another embodiment of a wearable device 1700 in the form of a helmet showing a back view. FIG. 19 illustrates a third embodiment of a wearable device 1700 in the form of a helmet with the cable 1706 leading to a wearable garment 1708 (such as a vest or partial vest) that can include a battery or a hub. Alternatively or additionally, the wearable device 1700 can include a crest 1710 or other protrusion for placement of the hub or battery.

Figure 20:
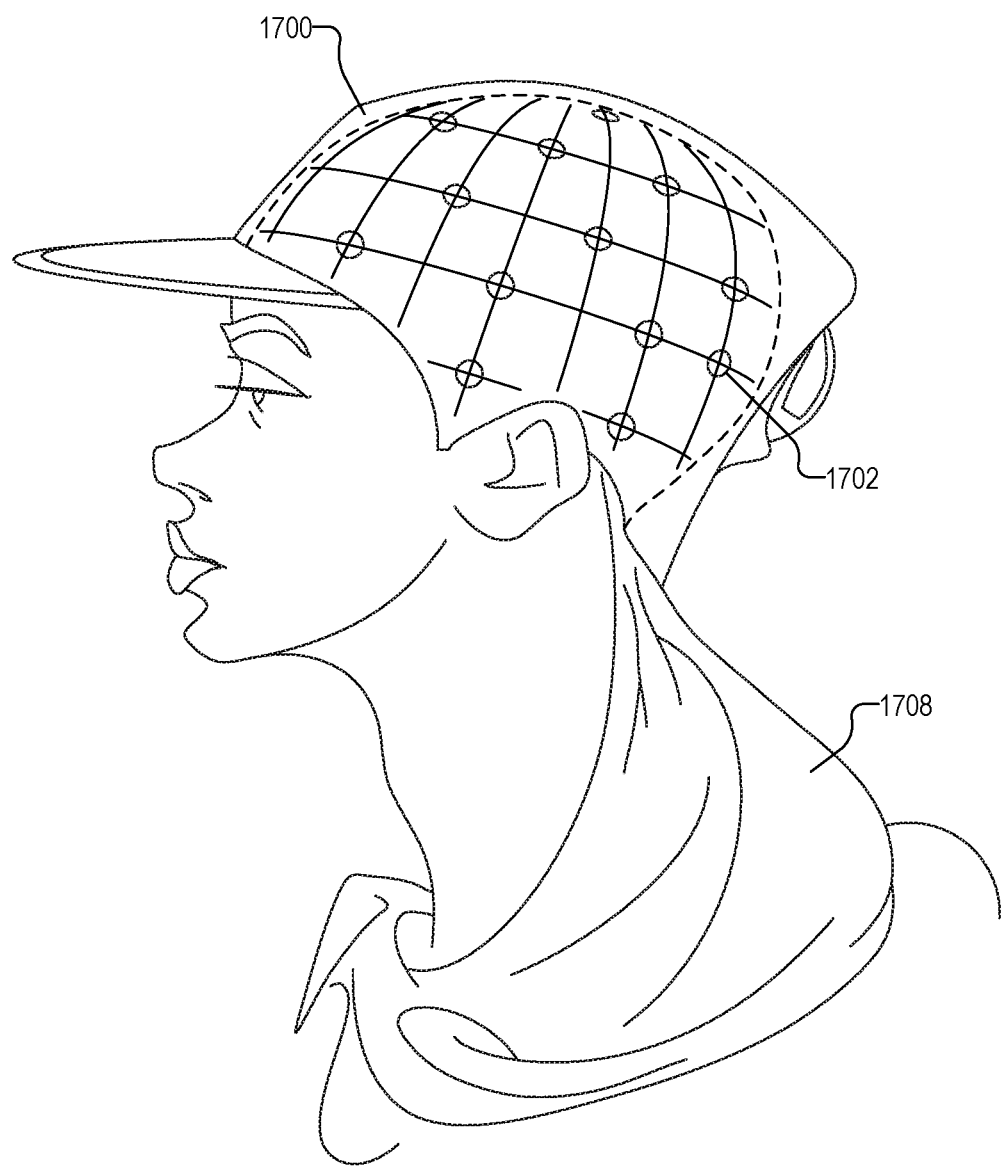
Figure 21:
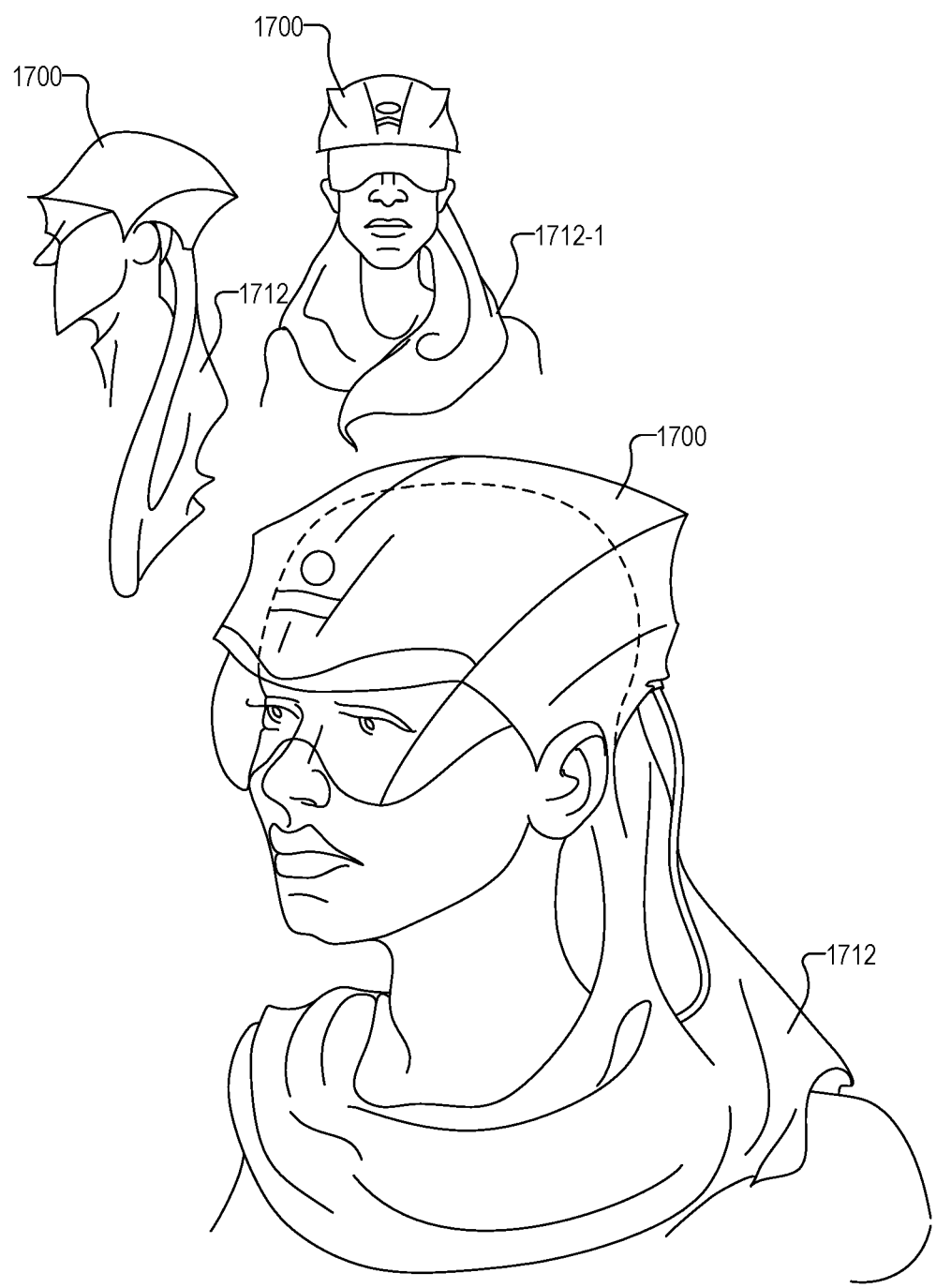
Figure 22:
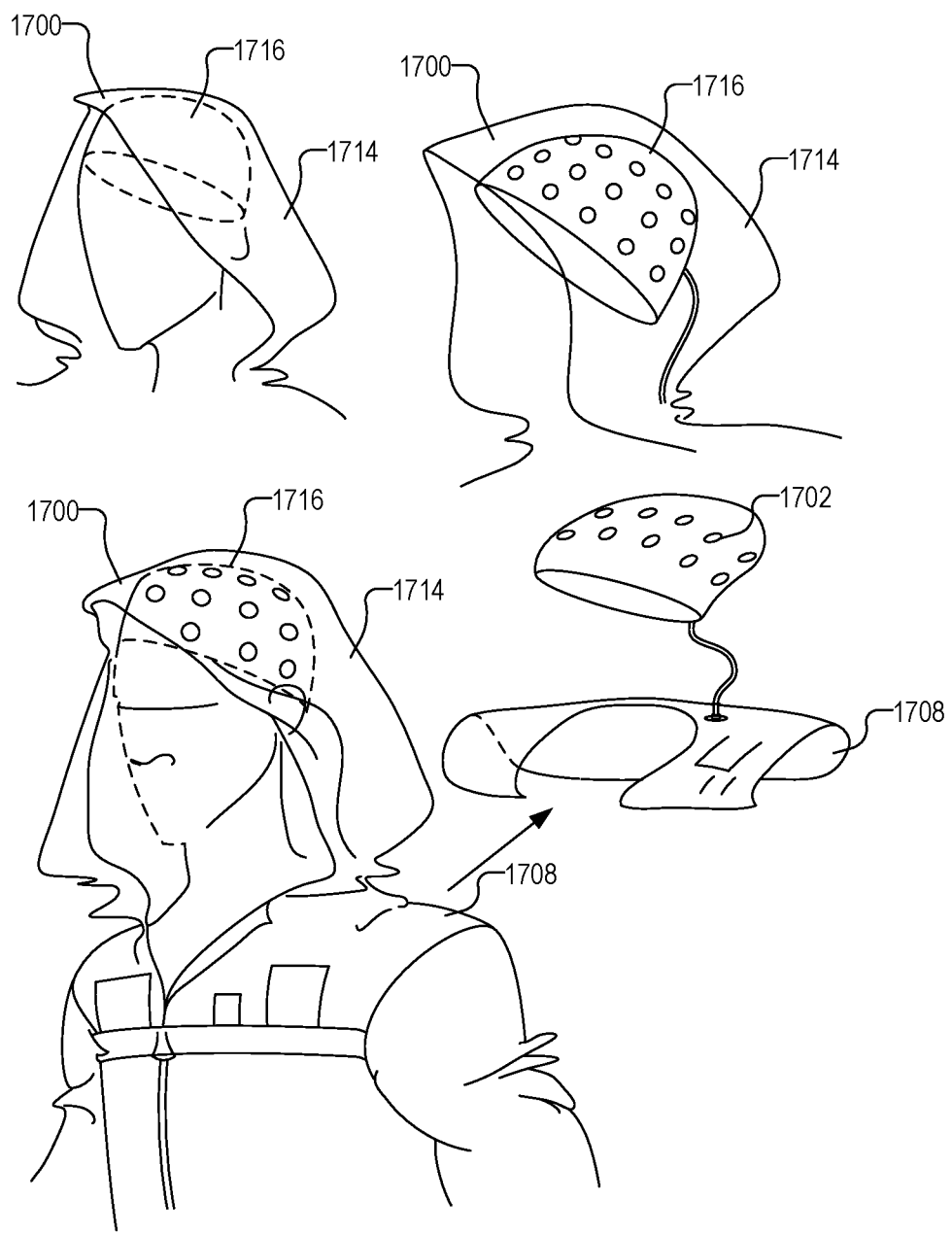

FIG. 20 illustrates another embodiment of a wearable device 1700 in the form of a cap with a wearable garment 1708 in the form of a scarf that may contain or conceal a cable, battery, and/or hub. FIG. 21 illustrates additional embodiments of a wearable device 1700 in the form of a helmet with a one-piece scarf 1712 or two-piece scarf 1712-1. FIG. 22 illustrates an embodiment of a wearable device 1700 that includes a hood 1714 and a beanie 1716 which contains the modules 1702, as well as a wearable garment 1708 that may contain a battery or hub.

Figure 23:
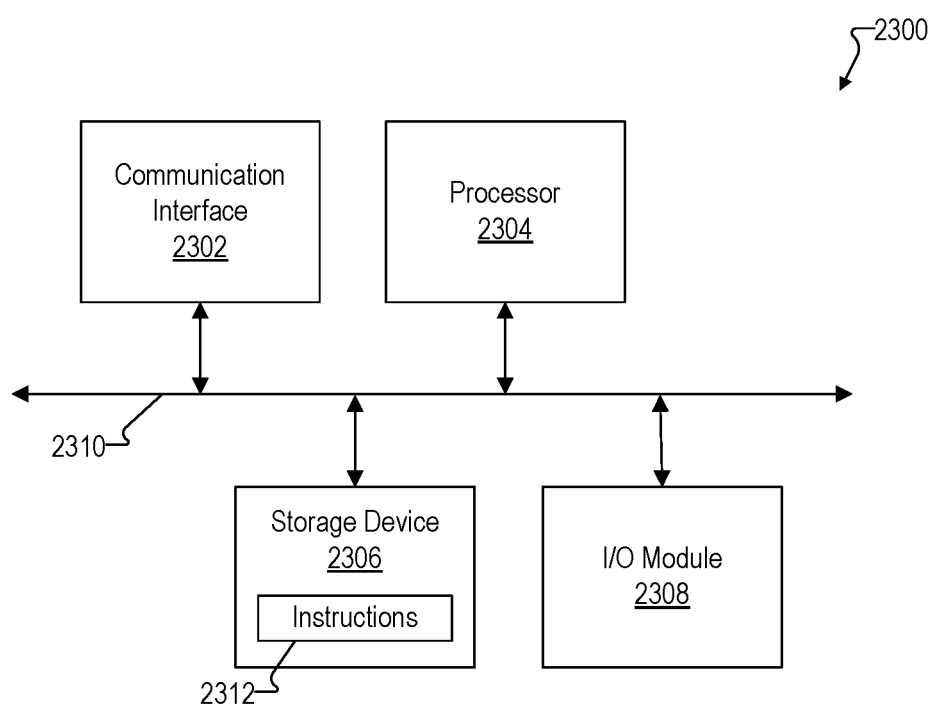
FIG. 23 illustrates an exemplary computing device.

FIG. 23 illustrates an exemplary computing device 2300 that may be specifically configured to perform one or more of the processes described herein. Any of the systems, units, computing devices, and/or other components described herein may be implemented by computing device 2300.

As shown in FIG. 23, computing device 2300 may include a communication interface 2302, a processor 2304, a storage device 2306, and an input/output ("I/O") module 2308 communicatively connected one to another via a communication infrastructure 2310. While an exemplary computing device 2300 is shown in FIG. 23, the components illustrated in FIG. 23 are not intended to be limiting. Additional or alternative components may be used in other embodiments. Components of computing device 2300 shown in FIG. 23 will now be described in additional detail.

Communication interface 2302 may be configured to communicate with one or more computing devices. Examples of communication interface 2302 include, without limitation, a wired network interface (such as a network interface card), a wireless network interface (such as a wireless network interface card), a modem, an audio/video connection, and any other suitable interface.

Processor 2304 generally represents any type or form of processing unit capable of processing data and/or interpreting, executing, and/or directing execution of one or more of the instructions, processes, and/or operations described herein. Processor 2304 may perform operations by executing computer-executable instructions 2312 (e.g., an application, software, code, and/or other executable data instance) stored in storage device 2306.

Storage device 2306 may include one or more data storage media, devices, or configurations and may employ any type, form, and combination of data storage media and/or device as described herein. Electronic data, including data described herein, may be temporarily and/or permanently stored in storage device 2306. For example, data representative of computer-executable instructions 2312 configured to direct processor 2304 to perform any of the operations described herein may be stored within storage device 2306. In some examples, data may be arranged in one or more databases residing within storage device 2306.

I/O module 2308 may include one or more I/O modules configured to receive user input and provide user output. I/O module 2308 may include any hardware, firmware, software, or combination thereof supportive of input and output capabilities. For example, I/O module 2308 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 2308 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 2308 is configured to provide graphical data to a display for presentation to a user. The graphical data may be representative of one or more graphical user interfaces and/or any other graphical content as may serve a particular implementation.

An illustrative optical measurement system includes a light source configured to emit a light pulse directed at a target. The optical measurement system further includes a control circuit configured to drive the light source with a current pulse comprising a non-linear rise, and a decline from a maximum output to zero having a duration within a threshold percentage of a total pulse duration of the current pulse.

An illustrative optical measurement system includes a light source configured to emit a light pulse directed at a target. The optical measurement system further includes a control circuit configured to drive the light source, the control circuit comprising a driver circuit comprising a rectangular pulse voltage source, a pull-up transistor, and a pull-down transistor.

An illustrative wearable system for use by a user includes a component, e.g. module unit, configured to be attached to a body of the user. The module unit comprises a light source configured to emit a light pulse directed at a target within the body, and at least one detector configured to detect photons of light after the light pulse is scattered by the target. The system further comprises a control circuit configured to drive the light source with a current pulse comprising a non-linear rise, and a decline from a maximum output to zero having a duration within a threshold percentage of a total pulse duration.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
  a light source configured to emit a light pulse directed at a target; and
  a control circuit configured to drive the light source with a current pulse comprising:
    a non-linear rise, and
    a decline from a maximum output to zero having a duration within a threshold percentage of a total pulse duration of the current pulse, wherein the threshold percentage is twenty percent.

2. The optical measurement system of claim 1, wherein the non-linear rise comprises an exponential rise.

3. The optical measurement system of claim 1, wherein the current pulse is configured to be within a threshold variance from a pulse defined by $$I(t) = \frac{eVN_{th}}{\tau_N \sinh(T/\tau_N)} \exp(t/\tau_N),$$

where e is an elementary charge constant, V is a volume of an active region of the light source, $N_{th}$ is a lasing threshold carrier density of the light source, T is the total pulse duration, and $\tau_N$ is a growth rate constant of the light source.

4. The optical measurement system of claim 1, wherein the control circuit comprises a driver circuit comprising:
  a rectangular pulse voltage source;
  a pull-up transistor; and
  a pull-down transistor.

5. The optical measurement system of claim 4, wherein the control circuit further comprises a capacitor configured to be coupled in parallel with the light source.

6. The optical measurement system of claim 4, wherein the driver circuit further comprises:
   a first resistor coupled to the rectangular pulse voltage source and the pull-down transistor;
   a diode coupled in parallel to the first resistor;
   a second resistor coupled to the rectangular pulse voltage source and the pull-up transistor; and
   a capacitor coupled in parallel with the pull-down transistor.

7. The optical measurement system of claim 4, wherein the control circuit further comprises:
   a reverse diode coupled in parallel to the light source;
   a resonant circuit comprising an inductor and a capacitor coupled to the driver circuit; and
   at least one additional resonant circuit comprising an additional inductor and an additional capacitor coupled in parallel to the resonant circuit.

8. The optical measurement system of claim 4, wherein the control circuit further comprises a nonlinear inductor.

9. The optical measurement system of claim 1, further comprising:
   at least one detector configured to detect arrival times of photons of the light pulse after the light pulse is scattered by the target; and
   a processing unit configured to:
      generate, based on the arrival times of the photons at the at least one detector, histogram data associated with the target; and
      determine, based on the histogram data, a property of the target.

10. The optical measurement system of claim 9, wherein the at least one detector comprises a single photon avalanche diode (SPAD).

11. The optical measurement system of claim 9, wherein the at least one detector is included in a wearable device configured to be worn by a user.

12. The optical measurement system of claim 11, wherein the wearable device includes a head-mountable component configured to be worn on a head of the user.

13. An optical measurement system comprising:
   a light source configured to emit a light pulse directed at a target; and
   a control circuit configured to drive the light source, the control circuit comprising a nonlinear inductor and a driver circuit comprising:
      a rectangular pulse voltage source;
      a pull-up transistor; and
      a pull-down transistor.

14. The optical measurement system of claim 13, wherein the control circuit further comprises a capacitor configured to be coupled in parallel with the light source.

15. The optical measurement system of claim 13, wherein the driver circuit further comprises:
   a first resistor coupled to the rectangular pulse voltage source and the pull-down transistor;
   a diode coupled in parallel to the first resistor;
   a second resistor coupled to the rectangular pulse voltage source and the pull-up transistor; and
   a capacitor coupled in parallel with the pull-down transistor.

16. The optical measurement system of claim 13, wherein the control circuit further comprises:
   a reverse diode coupled in parallel to the light source; and
   a resonant circuit comprising an inductor and a capacitor coupled to the driver circuit; and
   at least one additional resonant circuit comprising an additional inductor and an additional capacitor coupled in parallel to the resonant circuit.

17. The optical measurement system of claim 13, wherein the control circuit is configured to drive the light source with a current pulse comprising:
   a non-linear rise, and
   a decline from a maximum output to zero having a duration within a threshold percentage of a total pulse duration of the current pulse.

18. The optical measurement system of claim 17, wherein the threshold percentage is twenty percent.

19. The optical measurement system of claim 17, wherein the non-linear rise comprises an exponential rise.

20. The optical measurement system of claim 17, wherein the current pulse is configured to be within a threshold of a pulse defined by $$I(t) = \frac{eVN_{th}}{\tau_N \sinh(T/\tau_N)} \exp(t/\tau_N),$$

where e is an elementary charge constant, V is a volume of an active region of the light source, $N_{th}$ is a lasing threshold carrier density of the light source, T is the total pulse duration, and $\tau_N$ is a growth rate constant of the light source.

21. The optical measurement system of claim 13, further comprising:
   at least one detector configured to detect arrival times of photons of the light pulse after the light pulse is scattered by the target; and
   a processing unit configured to:
      generate, based on the arrival times of the photons at the at least one detector, histogram data associated with the target; and
      determine, based on the histogram data, a property of the target.

22. The optical measurement system of claim 21, wherein the at least one detector comprises a single photon avalanche diode (SPAD).

23. The optical measurement system of claim 21, wherein the at least one detector is included in a wearable device configured to be worn by a user.

24. The optical measurement system of claim 23, wherein the wearable device includes a head-mountable component configured to be worn on a head of the user.

25. A wearable system for use by a user comprising:
   a module unit configured to be attached to a body of the user, the module unit comprising:
      a light source configured to emit a light pulse directed at a target within the body, and
      at least one detector configured to detect photons of light after the light pulse is scattered by the target; and
   a control circuit configured to drive the light source with a current pulse comprising:
      a non-linear rise, and
      a decline from a maximum output to zero having a duration within a threshold percentage of a total pulse duration, wherein the threshold percentage is twenty percent.

26. The wearable system of claim 25, wherein the nonlinear rise comprises an exponential rise.

27. The wearable system of claim 25, wherein the current pulse is configured to be within a threshold variance from a pulse defined by $$I(t) = \frac{eVN_{th}}{\tau_N \sinh(T/\tau_N)} \exp(t/\tau_N),$$

where e is an elementary charge constant, V is a volume of an active region of the light source, $N_{th}$ is a lasing threshold carrier density of the light source, T is the total pulse duration, and $\tau_N$ is a growth rate constant of the light source.

28. The wearable system of claim 25, wherein the control circuit comprises a driver circuit comprising:
a rectangular pulse voltage source;
a pull-up transistor; and
a pull-down transistor.

29. The wearable system of claim 28, wherein the control circuit further comprises a capacitor configured to be coupled in parallel with the light source.

30. The wearable system of claim 28, wherein the driver circuit further comprises:
a first resistor coupled to the rectangular pulse voltage source and the pull-down transistor;
a diode coupled in parallel to the first resistor;
a second resistor coupled to the rectangular pulse voltage source and the pull-up transistor; and
a capacitor coupled in parallel with the pull-down transistor.

31. The wearable system of claim 28, wherein the control circuit further comprises:
a reverse diode coupled in parallel to the light source; and
a resonant circuit comprising an inductor and a capacitor coupled to the driver circuit;
at least one additional resonant circuit comprising an additional inductor and an additional capacitor coupled in parallel to the resonant circuit.

32. The wearable system of claim 28, wherein the control circuit further comprises a nonlinear inductor.

33. The wearable system of claim 25, wherein:
the at least one detector is further configured to detect arrival times of the photons of the light after the light pulse is scattered by the target; and
the wearable system further comprises a processing unit configured to:
generate, based on the arrival times of the photons at the at least one detector, histogram data associated with the target; and
determine, based on the histogram data, a property of the target.

34. The wearable system of claim 25, wherein the at least one detector comprises a single photon avalanche diode (SPAD).

35. The wearable system of claim 25, wherein the module unit is configured to be worn on a head of the user.

* * * * *